(12) United States Patent
Opperman

(10) Patent No.: US 11,148,988 B2
(45) Date of Patent: Oct. 19, 2021

(54) CANNABINOID PROCESSING METHODS AND SYSTEMS

(71) Applicant: Marquette Analytica, Royal Oak, MI (US)

(72) Inventor: Robert Opperman, Midland, MI (US)

(73) Assignee: Marquette Analytica, Midland, MI (US)

(*) Notice: Subject to any disclaimer, the term of this patent is extended or adjusted under 35 U.S.C. 154(b) by 0 days.

(21) Appl. No.: 17/025,260

(22) Filed: Sep. 18, 2020

(65) Prior Publication Data

US 2021/0101856 A1 Apr. 8, 2021

Related U.S. Application Data

(60) Provisional application No. 62/903,497, filed on Sep. 20, 2019, provisional application No. 62/926,555, filed on Oct. 27, 2019, provisional application No. 62/948,217, filed on Dec. 14, 2019, provisional application No. 62/952,360, filed on Dec. 22, 2019.

(51) Int. Cl.
| | | |
|---|---|---|
| *C07C 37/84* | (2006.01) | |
| *A23P 10/00* | (2016.01) | |
| *B01D 9/00* | (2006.01) | |
| *C07C 37/68* | (2006.01) | |
| *A23P 30/40* | (2016.01) | |
| *A23P 10/20* | (2016.01) | |
| *A23L 33/105* | (2016.01) | |
| *C07C 37/86* | (2006.01) | |
| *C07C 39/21* | (2006.01) | |

(52) U.S. Cl.
CPC ............ *C07C 37/84* (2013.01); *A23L 33/105* (2016.08); *A23P 10/20* (2016.08); *A23P 30/40* (2016.08); *B01D 9/0054* (2013.01); *B01D 9/0059* (2013.01); *C07C 37/685* (2013.01); *C07C 37/86* (2013.01); *B01D 2009/0086* (2013.01); *C07C 39/21* (2013.01)

(58) Field of Classification Search
CPC ....... C07C 37/84; C07C 37/86; C07C 37/685; A23P 10/20
See application file for complete search history.

(56) References Cited

U.S. PATENT DOCUMENTS

| | | | |
|---|---|---|---|
| 10,155,176 B1 * | 12/2018 | Feuer | B01D 69/02 |
| 10,595,474 B2 * | 3/2020 | Leo | A01G 9/246 |
| 10,925,853 B2 * | 2/2021 | Bruun | A61K 31/352 |
| 2019/0241536 A1 * | 8/2019 | Durkacz | C07C 37/70 |

* cited by examiner

*Primary Examiner* — Sikarl A Witherspoon

(57) ABSTRACT

A system and method for crystallization and pelleting of a cannabinoid, including cannabidiol (CBD).

10 Claims, 8 Drawing Sheets

CANNABINOID PROCESSING METHODS AND SYSTEMS

CROSS-REFERENCE TO RELATED PATENT APPLICATIONS

This patent application claims priority to U.S. Provisional Patent Application No. 62/903,497, filed Sep. 20, 2019; U.S. Provisional Patent Application No. 62/926,555, filed Oct. 27, 2019; U.S. Provisional Patent Application No. 62/948,217, filed Dec. 14, 2019; U.S. Provisional Patent Application No. 62/952,360, filed Dec. 22, 2019, the disclosures of each of which are herein incorporated in their entirety.

BACKGROUND

*Cannabis* has been used as a source of fiber to make paper and clothing, as a recreational drug, and in traditional medicine. In recent years, compounds present in *Cannabis*, including the cannabinoids $\Delta^9$-tetrahydrocannabinol (THC) and cannabidiol (CBD), have been shown to alleviate inflammation and cancer-related symptoms. See, e.g., Federica Pellati et al., *Cannabis sativa L. and Nonpsychoactive Cannabinoids: Their Chemistry and Role against Oxidative Stress, Inflammation, and Cancer*, BIOMED RES. INT'L, 2018.

Historically, *Cannabis* has been divided into three species: *Cannabis sativa*, *Cannabis indica*, and *Cannabis ruderalis*. These species have been extensively hybridized, and the resulting hybrids are classified as *C. sativa* and can be further characterized by chemotype according to the cannabinoid profile. *Cannabis* plants having high THC levels are often used for medicinal properties. In contrast, *Cannabis* plants having low THC levels (hemp) and high CBD levels have been used in textiles and foods.

The increased interest in CBD as well as the lift of the ban on industrial hemp (cannabis having a THC content of less than 0.3%) in the United States and Europe has made industrial hemp an attractive source of fiber, cannabinoids, and other phytochemicals. In addition to cannabinoids, *Cannabis* plants contain cannabinoid acids, terpenes, flavonoids, carbohydrates, fatty acids, fatty acid esters, amides, amines, phytosterols, and phenolic compounds. *Cannabis*-derived terpenes impart *Cannabis*'s distinctive smell and have been shown to reduce cytokines associated with peripheral inflammation. Interest in CBD has grown, because it is non-psychoactive and elicits antioxidant, anti-inflammatory, antibiotic, neuroprotective, anxiolytic, and anticonvulsant properties. For example, the United States Food and Drug Administration (FDA) approved synthetic cannabidiol (EPIDIOLEX®) for the treatment of seizures associated with Lennox-Gastaut syndrome or Dravet syndrome in children. FDA News Release Jun. 25, 2018. Furthermore, research into derivatives of compounds from *Cannabis* plants require large amounts of each starting material. However, there have been challenges in extracting these compounds in high yields and purity.

There exists a need for more efficient methods of rapid preparation of purified cannabinoid crystals with high yields and purity, substantially free from contaminants, for use in medicine.

SUMMARY

The disclosure provides, among other things, methods of preparing cannabinoid, e.g., cannabidiol, crystals that advantageously increase cannabinoid, e.g., cannabidiol, yield and purity but decrease process time from hours to minutes.

In one embodiment, the invention provides a method for decarboxylating cannabidiol-acid (CBDA) to form cannabidiol (CBD) comprising providing a cannabis extract to a heat transfer screw heat at a sufficient temperature to decarboxylate the cannabidiol-acid (CBDA) to form cannabidiol (CBD); moving the heated cannabis extract through the heat transfer screw for about 1-60 minutes to produce a CBD foam; extruding the heated CBD foam into a vessel and passing pentane at a temperature of −20° C. to 20° C. over the heated CBD foam to extract terpenes and other cannabinoids; and recovering the cannabidiol crystals.

In one embodiment, the invention provides a method for crystallizing cannabidiol (CBD) comprising providing the cannabidiol extract to a heat transfer screw heat at a sufficient temperature; moving the heated cannabidiol extract through the heat transfer screw for about 1-60 minutes; introducing an foaming agent to produce a CBD foam; extruding the heated CBD foam into a vessel and passing an anti-solvent at a temperature of −20° C. to 20° C. over the heated CBD foam to extract terpenes and other cannabinoids; and recovering the cannabidiol crystals. In one embodiment, anti-solvent may be a hydrocarbon. The hydrocarbon may be hexane, pentane, butane, or propane. In an embodiment, the foaming agent may be a gas, e.g., nitrogen, carbon dioxide ($CO_2$), or helium. In one embodiment, the foaming agent may be a blowing agent. In one embodiment, the blowing agent may be carbon dioxide ($CO_2$), butane, propane, or a chlorofluorocarbon. The foaming agent acts to increase the surface area of the CBD foam to allow for the extraction of terpenes by the anti-solvent.

In an embodiment, a system for crystallizing cannabidiol may comprise a heat transfer screw heat configured to be heated to a sufficient temperature comprising means for introducing a foaming agent and in fluid connection with a vessel configured to pass an anti-solvent at a temperature of −20° C. to 20° C. from the proximal end of the heat transfer screw to the distal end, and means for collecting the anti-solvent. In one embodiment, anti-solvent may be a hydrocarbon, including but not limited to pentane, butane, propane, or hexane.

In one embodiment, the invention provides a method for decarboxylating a cannabinoid acid comprising providing a cannabis extract to a heat transfer screw heat at a sufficient temperature to decarboxylate the cannabinoid acid to form a cannabinoid; moving the heated cannabis extract through the heat transfer screw for about 1-60 minutes to produce a cannabinoid foam; extruding the heated cannabinoid foam into a vessel and passing pentane at a temperature of −20° C. to 20° C. over the heated cannabinoid foam to extract terpenes; and recovering the cannabinoid crystals.

In one embodiment, the invention provides a method for crystallizing a cannabinoid comprising providing a cannabinoid extract to a heat transfer screw heat at a sufficient temperature; moving the heated cannabinoid extract through the heat transfer screw for about 1-60 minutes; introducing an foaming agent to produce a cannabinoid foam; extruding the heated cannabinoid foam into a vessel and passing an anti-solvent at a temperature of −20° C. to 20° C. over the heated cannabinoid foam to extract terpenes; and recovering the cannabinoid crystals. In one embodiment, anti-solvent may be a hydrocarbon. The hydrocarbon may be hexane, pentane, butane, or propane. In an embodiment, the foaming agent may be a gas, e.g., nitrogen, carbon dioxide ($CO_2$), or helium. In an embodiment, the gas may be an inert gas, including but not limited to helium, neon, argon, krypton, xenon, radon, or a mixture thereof. In one embodiment, the foaming agent may be a blowing agent. In one embodiment, the blowing agent may be carbon dioxide ($CO_2$), butane, propane, a hydro-fluoro-olefin (HFO), or a chlorofluorocarbon. The foaming agent acts to increase the surface area of the cannabinoid foam to allow for the extraction of terpenes by the anti-solvent.

In an embodiment, a system for crystallizing cannabinoid may comprise a heat transfer screw heat configured to be heated to a sufficient temperature comprising means for introducing a foaming agent and in fluid connection with a vessel configured to pass an anti-solvent at a temperature of −20° C. to 20° C. from the proximal end of the heat transfer screw to the distal end, and means for collecting the anti-solvent. In one embodiment, anti-solvent may be a hydrocarbon, including but not limited to pentane, butane, propane, or hexane.

In an embodiment, a method of preparing a cannabinoid extract may comprise: providing a cannabis extract to a heating means, optionally comprising a substantially flat surface or a heat transfer screw conveyor; supplying sufficient heat to the surface with the cannabis extract to decarboxylate the cannabinoid acid to form cannabinoid; moving the heated cannabis extract comprising cannabinoid to a crystallization vessel; solubilizing the heated cannabis extract comprising cannabinoid and terpenes in a first solvent at a ratio between 1:1 and 1:5 of cannabis extract to first solvent; precipitating cannabinoid crystals and form a solvent/cannabinoid crystal slurry; filtering the solvent/cannabinoid crystal slurry through a filter, optionally a membrane, to produce a first permeate and a first retentate; wherein the first permeate comprises the first solvent, and the first retentate comprises the cannabinoid crystals; recovering the cannabinoid crystals; and filtering the first permeate through a second membrane to produce to a second permeate and a second retentate, wherein the second permeate comprises first solvent and the second retentate comprises the terpenes.

In one embodiment, a method of preparing a cannabinoid extract may comprise providing a cannabis extract to a heating means, optionally comprising a heated substantially flat platform or a heat transfer screw conveyor; supplying sufficient heat to the surface with the cannabis extract to decarboxylate the cannabinoid acid to form cannabinoid; moving the heated cannabis extract comprising cannabinoid and terpenes to a crystallization vessel; solubilizing the heated cannabis extract comprising cannabinoid in a first solvent at a ratio between 1:1 and 1:5 of cannabis extract to first solvent; adding a sufficient amount of a second solvent at a ratio between 1:1 and 10:1 of second solvent to first solvent to precipitate cannabinoid crystals and form a solvent/cannabinoid crystal slurry; filtering the solvent/cannabinoid crystal slurry through a filter, optionally a first membrane, to produce a first permeate and a first retentate; wherein the first permeate comprises the first and second solvents, and the first retentate comprises the cannabinoid crystals; recovering the cannabinoid crystals; and filtering the first permeate through a second membrane to produce to a second permeate and a second retentate, wherein the second permeate comprises the second solvent and the second retentate comprises the first solvent.

In one embodiment, a method of preparing a cannabinoid extract may comprise placing a cannabis extract on a surface; supplying sufficient heat to the surface with the cannabis extract to decarboxylate the cannabinoid acid to form cannabinoid; moving the heated cannabis extract comprising cannabinoid to a crystallization vessel; solubilizing the heated cannabis extract comprising cannabinoid in a first solvent at a ratio between 1:1 and 1:5 of cannabis extract to first solvent; adding a sufficient amount of a nucleating agent and second solvent at a ratio between 1:1 and 10:1 of second solvent to first solvent to precipitate cannabinoid crystals and form a solvent/cannabinoid crystal slurry; filtering the solvent/cannabinoid crystal slurry through a filter, optionally a first membrane, to produce a first permeate and a first retentate; wherein the first permeate comprises the first and second solvents, and the first retentate comprises the cannabinoid crystals; recovering the cannabinoid crystals; and filtering the first permeate through a second membrane to produce to a second permeate and a second retentate, wherein the second permeate comprises the second solvent and the second retentate comprises the first solvent.

The invention also provides a system for decarboxylating a cannabinoid comprising a heat transfer screw heat configured to be heated to a sufficient temperature; a means for adding a foaming agent to the heat transfer screw; in fluid connection with a vessel configured to pass anti-solvent at a temperature of −20° C. to 20° C. from the proximal end of the heat transfer screw to the distal end, and means for collecting the anti-solvent.

In an embodiment, a system for decarboxylating cannabinoid acid may comprise a heating means configured to move heated product into a crystallization vessel, wherein the crystallization vessel is configured with a first solvent input, a second solvent input, a nucleating agent input, heat product input, and further comprising agitation means, coupled to a first membrane filtration means coupled to a solvent storage means coupled to second membrane filtration means, wherein the second membrane filtration means comprises a first solvent output and a second solvent output.

In an embodiment, a method for decarboxylating and crystallizing a cannabinoid acid comprising: placing a cannabis extract comprising a cannabinoid acid in a heating means, optionally comprising a heated surface or a heat transfer screw conveyor; supplying sufficient heat to the surface with the cannabis extract to decarboxylate the cannabinoid acid to form cannabinoid; moving the heated cannabis extract comprising cannabinoid to a crystallization vessel; solubilizing the heated cannabis extract comprising cannabinoid and terpenes in a first solvent at a ratio between 1:1 and 1:5 of cannabis extract to first solvent; precipitating cannabinoid crystals and form a solvent/cannabinoid crystal slurry; filtering the solvent/cannabinoid crystal slurry through a filter, optionally a first membrane, to produce a first permeate and a first retentate; wherein the first permeate comprises the first solvent, and the first retentate comprises the cannabinoid crystals; recovering the cannabinoid crystals; and filtering the first permeate through a second membrane to produce to a second permeate and a second retentate, wherein the second permeate comprises first solvent and the second retentate comprises the terpenes.

In an embodiment, a method for decarboxylating and crystallizing a cannabinoid may comprise supplying sufficient heat to a cannabis extract comprising a cannabinoid acid to decarboxylate the cannabinoid acid to form a cannabinoid; moving the heated cannabis extract comprising cannabinoid to a crystallization vessel; solubilizing the heated cannabis extract comprising cannabinoid and terpenes in a first solvent at a ratio between 1:1 and 1:5 of cannabis extract to first solvent; precipitating cannabinoid crystals and form a solvent/cannabinoid crystal slurry; filtering the solvent/cannabinoid crystal slurry through a filter, optionally a first membrane, to produce a first permeate and a first retentate; wherein the first permeate comprises the first solvent, and the first retentate comprises the cannabinoid crystals; recovering the cannabinoid crystals; and filtering the first permeate through a membrane to produce to a second permeate and a second retentate, wherein the second permeate comprises first solvent and the second retentate comprises the terpenes.

In an embodiment, a method for decarboxylating and crystallizing a cannabinoid may comprise supplying sufficient heat to a cannabis extract comprising a cannabinoid acid to decarboxylate the cannabinoid acid to form a cannabinoid; moving the heated cannabis extract comprising cannabinoid and terpenes to a crystallization vessel; solubilizing the heated cannabis extract comprising cannabinoid in a first solvent at a ratio between 1:1 and 1:5 of cannabis extract to first solvent; adding a sufficient amount of a second solvent at a ratio between 1:1 and 10:1 of second solvent to first solvent to precipitate cannabinoid crystals and form a solvent/cannabinoid crystal slurry; filtering the solvent/cannabinoid crystal slurry through a filter, optionally a first membrane, to produce a first permeate and a first retentate; wherein the first permeate comprises the first and second solvents, and the first retentate comprises the cannabinoid crystals; recovering the cannabinoid crystals; and filtering the first permeate through a membrane to produce to a second permeate and a second retentate, wherein the second permeate comprises the second solvent and the second retentate comprises the first solvent.

In one embodiment, a method for decarboxylating and crystallizing a cannabinoid may comprise supplying sufficient heat to a cannabis extract comprising a cannabinoid acid to decarboxylate the cannabinoid acid to form a cannabinoid; moving the heated cannabis extract comprising cannabinoid to a crystallization vessel; solubilizing the heated cannabis extract comprising cannabinoid in a first solvent at a ratio between 1:1 and 1:10 of cannabis extract to first solvent; adding a sufficient amount of a nucleating agent and second solvent at a ratio between 1:1 and 20:1 of second solvent to first solvent to precipitate cannabinoid crystals and form a solvent/cannabinoid crystal slurry; filtering the solvent/cannabinoid crystal slurry through a filter, optionally a first membrane, to produce a first permeate and a first retentate; wherein the first permeate comprises the first and second solvents, and the first retentate comprises the cannabinoid crystals; recovering the cannabinoid crystals; and filtering the first permeate through a membrane to produce to a second permeate and a second retentate, wherein the second permeate comprises the second solvent and the second retentate comprises the first solvent.

DETAILED DESCRIPTION

Medical *Cannabis* and Cannabinoids

Figure 1A:
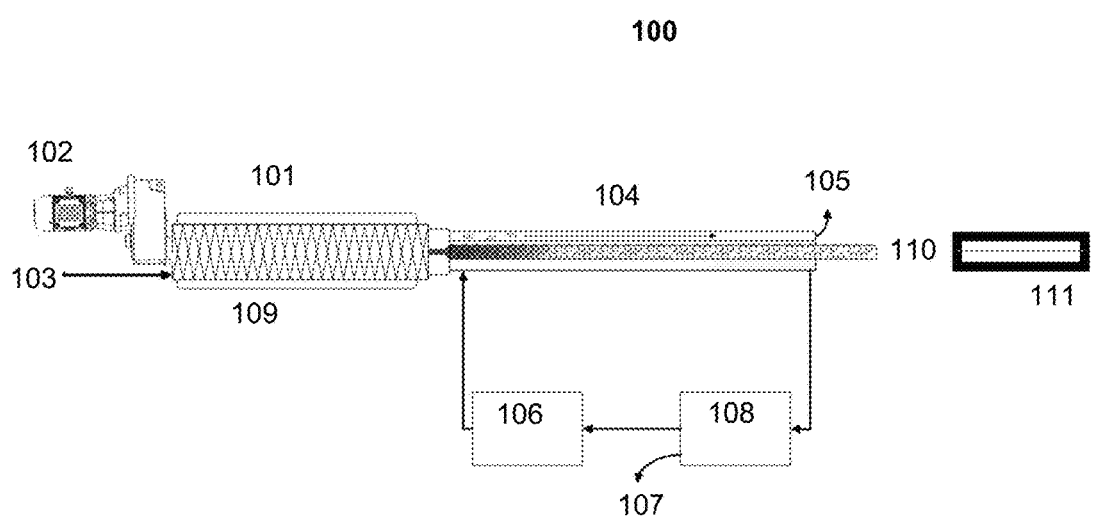
FIG. 1A-C depicts exemplary schematics of systems for decarboxylation and crystallization of a cannabinoid.

Medical cannabis has been used to alleviate the symptoms of patients suffering from a variety of medical conditions including cancer, anorexia, AIDS, chronic pain, spasticity, glaucoma, arthritis, and migraines. For example, the anti-emetic properties of *Cannabis* have been useful in the treatment of nausea and vomiting in cancer patients undergoing chemotherapy as well as in the treatment of weight loss syndrome associated with AIDS. Glaucoma patients have been treated with *Cannabis* to reduce intraocular pressure. Muscle relaxing and anticonvulsant effects of *Cannabis* have also been reported.

However, consumption of the whole *Cannabis* plant, e.g., by smoking, has also results in side-effect including impaired cognitive functions, perception, reaction time, learning, and memory. To mitigate such side-effects, there is growing interest in investigating the medicinal properties of individual *Cannabis*-derived compounds and sub-combinations and derivatives thereof. In addition, many potential patients have personal or religious objections to consuming cannabis in plant form. To address these issues, there is a great interest in developing a pharmaceutical form of cannabis extracts, especially crystallize extracts. The disclosure relates to methods of preparing cannabis extracts that can be useful in such applications.

Cannabinoids are synthesized primarily in the glandular trichomes of *Cannabis* plants and include tetrahydrocannabinolic acid, $\Delta^8$ tetrahydrocannabinolic acid, $\Delta^9$ tetrahydrocannabinolic acid, tetrahydrocannabinol, $\Delta^8$ tetrahydrocannabinol, $\Delta^9$ tetrahydrocannabinol (THC), cannabidiolic acid, cannabidiol (CBD), cannabinol, cannabigerolic acid, cannabigerol, cannabigerolic acid, cannabichromene, and tetrahydrocannabivarin, any of which can be obtained by the methods described herein.

Cannabinoid Decarboxylation and Crystallization

The disclosure generally relates to improved methods for cannabinoid crystallization. For example, the disclosure relates to the invention provides a method for crystallizing a cannabinoid, for example, cannabidiol (CBD), comprising providing a cannabinoid extract comprising a cannabinoid acid to a heat transfer screw heat at a sufficient temperature; moving the heated cannabinoid extract through the heat transfer screw for about 1-60 minutes; introducing an foaming agent to produce a cannabinoid foam; extruding the heated cannabinoid foam into a vessel and passing anti-solvent at a temperature of $-20°$ C. to $20°$ C. over the heated cannabinoid foam to extract terpenes; and recovering the cannabinoid crystals. The anti-solvent may be a hydrocarbon. The hydrocarbon may be hexane, pentane, butane, or propane. The foaming agent may be a blowing agent. The blowing agent may be carbon dioxide ($CO_2$), chlorofluorocarbons, or a mixture thereof. The cannabinoid crystals, e.g., CBD, produced by crystallization can be collected, tested, weighed, and packaged, preferably in nitrogen-flushed, light proof containers (e.g., vials or bags).

When decarboxylated, the cannabinoids increase substantially in viscosity. This makes it exceedingly difficult for any solvent or anti-solvent to contact the terpenes to solubilize them and subsequently remove them from the cannabinoid extract. Without wishing to be bound to a single theory, the inventor surprising discovered that introducing a blowing agent during the decarboxylation reaction has the effect of creating more surface area for the anti-solvent to contact terpenes present in the crystal. This may be achieved by in situ production of carbon dioxide from the decarboxylation of the cannabinoid acid, where the decarboxylation vessel forces the carbon dioxide to create a foam out of the increasingly viscous cannabinoid. In other embodiments, an extraneous foaming agent may be introduced to produce a cannabinoid foam. Further, after the cannabinoid has been decarboxylated and crystallized, it may be subjected to ultrasonic cavitation to break the crystals into smaller pieces, increasing surface area, and increasing the extraction of any terpenes present. The ultrasonic cavitation may be done at a temperature of about −20° C. to 20° C.

The cannabinoid extract is passed through a heat transfer screw conveyor for 90° C. to 130° C. for 1-60 minutes. The heat transfer screw conveyor does not allow the ventilation of the $CO_2$ produced, instead, the $CO_2$ produced from decarboxylation serves as a foaming agent to create a heated cannabinoid foam. Alternatively, an extraneous foaming agent may be adding, including but not limited to a blowing agent, including but not limited to carbon dioxide ($CO_2$), pentane, chlorofluorocarbons, or a mixture thereof. The heat transfer screw conveyor is coupled to a solution tube where cold pentane at about −20° C. to 0° C. is passed over the heated cannabinoid foam. See FIG. 1A. The cold anti-solvent (e.g., pentane at about −20° C. to 0° C.) is fed in at the proximal end where the heated cannabinoid foam is extruded from the heat transfer screw conveyor and runs along the length of the heated cannabinoid foam, allowing the foaming agent (e.g., $CO_2$) to vent and allowing the anti-solvent (e.g., pentane) to absorb the terpenes. At the distal end, a cooled, cannabinoid crystal, substantially free of terpenes is extruded. The cannabinoid crystal may be a cannabidiol crystal substantially free of terpenes.

The cannabinoid crystals may be subjected to ultrasonic cavitation to break up the cannabinoid crystals. The sonication device may comprise one or several sonication devices providing ultrasonic cavitation. In one embodiment, several ultrasonic cavitation devices may be configured in an array.

The cannabinoid crystals produced by crystallization are collected by filtration and the solvent(s) may be subjected to membrane exchange to separate the solvent(s). In another embodiment, the cannabinoid crystals may be washed with additional solvent and dried. The cannabinoid crystals collected may be tested, weighed, and packaged, preferably in nitrogen-flushed, light proof containers (e.g., vials, jars, bags).

Temperature

The anti-solvent used in the decarboxylation and/or crystallization may be at any suitable temperature. The temperature can be between about −20° C. to about 40° C. In other examples, the temperature of the anti-solvent can be about −20° C., −19° C., −18° C., −17° C., −16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C. In other examples, the temperature of the anti-solvent can be between about −10° C. to 10° C., −10° C. to 0° C., −15° C. to 20° C., −20° C. to 20° C., or −15° C. to 5° C. The temperature in the system can be maintained by thermal insulation means.

Time

The cannabinoid extract may be decarboxylated and/or crystallization for any suitable amount of time, such as from about 1 minute to about 120 minutes. The cannabinoid extract can undergo crystallization and/or decarboxylation for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes. The cannabinoid extract can undergo crystallization and/or decarboxylation for 1-50 minutes, 5-50 minutes, 10-50 minutes, 25-35 minutes, 21-45 minutes, 20-40 minutes, 25-40 minutes, 30-40 minutes, 27-45 minutes, 29-39 minutes, 21-31 minutes, 23-32 minutes, 29-38 minutes, or 24-36 minutes. The cannabinoid extract can undergo crystallization and/or decarboxylation for about 1-60 minutes.

Cannabinoids

The cannabinoid extract, may comprise cannabidiol, tetrahydrocannabinol (THC), cannabidiol (CBD), cannabidiol acid (CBDA), cannabigerol, cannabinol, cannabichromene, cannabigerivarin, tetrahydrocannabivarin, cannabidivarin, cannabichromevarin, or a mixture thereof. It should be appreciated that the extract may comprise a cannabinoid acid, including but not limited to cannabigerolic acid, cannabidiol acid (CBDA), Δ9-tetrahydrocannabinolic acid (THCA), cannabidiolic acid, cannabichromenenic acid, cannabigerovarinic acid, tetrahydrocanabivarinic acid, cannabidivarinic acid, cannabichromevarinic acid, or a mixture thereof.

Cannabinoids present in a cannabinoid extract may include, but are not limited to, tetrahydrocannabinol, cannabidiol, cannabigerol, cannabinol, cannabichromene, cannabigerivarin, tetrahydrocannabivarin, cannabidivarin, cannabichromevarin, or a mixture thereof. It should be appreciated that the extract may also include cannabinoid acids, such as cannabigerolic acid, Δ9-tetrahydrocannabinolic acid, cannabidiolic acid, cannabichromenenic acid, cannabigerovarinic acid, tetrahydrocanabivarinic acid, cannabidivarinic acid, cannabichromevarinic acid, or a mixture thereof.

For example, the cannabinoid may be cannabigerolic acid (CBGA), Δ$^9$-tetrahydrocannabinolic acid (Δ$^9$-THC), cannabidiolic acid (CBDA), cannabichromenenic acid (CBCA), cannabigerovarinic acid (CBGVA), tetrahydrocanabivarinic acid (THCVA), cannabidivarinic acid (CBDVA), cannabichromevarinic acid (CBCVA), or a mixture thereof.

The cannabinoid may be a cannabichromene. For example, the cannabichromene may be cannabichromene (CBC), cannabichromenic acid (CBCA), cannabichromevarin (CBCV), cannabichromevarinic acid (CBCVA), or a mixture thereof.

The cannabinoid may be a cannabicyclol. For example, the cannabicyclol may be cannabicyclol (CBL), cannabicyclolic acid (CBLA), cannabicyclovarin (CBLV), or a mixture thereof.

The cannabinoid may be a cannabidiol. Cannabidiols include but are not limited to cannabidiol (CBD), cannabidiol monomethylether (CBDM), cannabidiolic acid (CBDA), cannabidiorcol (CBD-C1), cannabidivarin (CBDV), cannabidivarinic acid (CBDVA), or a mixture thereof.

The cannabinoid may be a cannabielsoin. For example, the cannabielsoin may be cannabielsoic acid B (CBEA-B), cannabielsoin (CBE), cannabielsoin acid A (CBEA-A), or a mixture thereof.

The cannabinoid may be a cannabigerol. Cannabigerols include but are not limited to cannabigerol (CBG), cannabigerol monomethylether (CBGM), cannabigerolic acid (CBGA), cannabigerolic acid monomethylether (CBGAM), cannabigerovarin (CBGV), cannabigerovarinic acid (CBGVA), or a mixture thereof.

The cannabinoid may be a cannabinol.

The cannabinoid may be a cannabinodiol. Cannabinodiols include, but are not limited to cannabinodiol (CBND), cannabinodivarin (CBVD), cannabinol (CBN), cannabinol methylether (CBNM), cannabinol-C2 (CBN-C2), cannabinol-C4 (CBN-C4), cannabinolic acid (CBNA), cannabiorcool (CBN-C1), cannabivarin (CBV), or a mixture thereof.

The cannabinoid may be a cannabitriol. Cannabitriols include but are not limited to 10-Ethoxy-9-hydroxy-delta-6a-tetrahydrocannabinol, 8,9-Dihydroxy-delta-6a-tetrahydrocannabinol, cannabitriol (CBT), cannabitriolvarin (CBTV), or a mixture thereof.

The cannabinoid may be a Δ-8-tetrahydrocannabinol. Δ-8-tetrahydrocannabinols include but are not limited to delta-8-tetrahydrocannabinol ($\Delta^8$-THC), delta-8-tetrahydrocannabinolic acid ($\Delta^8$-THCA), or a mixture thereof.

The cannabinoid may be a Δ-9-tetrahydrocannabinol. Δ-9-tetrahydrocannabinols include but are not limited to delta-9-tetrahydrocannabinol (delta-9 THC), delta-9-tetrahydrocannabinol-C4 (THC-C4), delta-9-tetrahydrocannabinolic acid A (THCA-A), delta-9-tetrahydrocannabinolic acid B (THCA-B), delta-9-tetrahydrocannabinolic acid-C4 (THCA-C4), delta-9-tetrahydrocannabiorcol (THC-C1), delta-9-tetrahydrocannabiorcolic acid (THCA-C1), delta-9-tetrahydrocannabivarin (THCV), delta-9-tetrahydrocannabivarinic acid (THCVA), or a mixture thereof.

The cannabinoid may be 10-Oxo-delta-6a-tetrahydrocannabinol (OTHC), cannabichromanon (CBCF), cannabifuran (CBF), cannabiglendol, cannabiripsol (CBR), cannbicitran (CBT), dehydrocannabifuran (DCBF), delta-9-cis-tetrahydrocannabinol (cis-THC), tryhydroxy-delta-9-tetrahydrocannabinol (triOH-THC), or a mixture thereof.

The cannabinoid may be cannabidiol (CBD).

The cannabinoid may be a tetrahydrocannabinol (THC), for example, delta-9-tetrahydrocannabinol, delta-8-tetrahydrocannabinol, or a combination thereof.

The concentration of a cannabinoid, for example, a cannabinoid acid, in the cannabinoid extract may range between about 0% (w/w) and about 50% (w/w), between about 5% (w/w) and about 45% (w/w), between about 10% (w/w) and about 40% (w/w), between about 15% (w/w) and about 35% (w/w), or between about 20% (w/w) and about 30% (w/w), inclusive. The cannabinoid concentration in the cannabinoid extract includes ranges of between about 0% (w/w) and about 5% (w/w), between about 5% (w/w) and about 10% (w/w), between about 10% (w/w) and about 15% (w/w), between about 15% (w/w) and about 20% (w/w), between about 20% (w/w) and about 25% (w/w), between about 25% (w/w) and about 30% (w/w), between about 30% (w/w) and about 35% (w/w), between about 35% (w/w) and about 40% (w/w), between about 40% (w/w) and about 45% (w/w), or between about 45% (w/w) and about 50% (w/w), inclusive. Therefore, the concentration of a cannabinoid in the cannabinoid extract can be between about 0% (w/w) and about 5% (w/w), between about 5% (w/w) and about 10% (w/w), between about 10% (w/w) and about 15% (w/w), between about 15% (w/w) and about 20% (w/w), between about 20% (w/w) and about 25% (w/w), between about 25% (w/w) and about 30% (w/w), between about 30% (w/w) and about 35% (w/w), between about 35% (w/w) and about 40% (w/w), between about 40% (w/w) and about 45% (w/w), between about 45% (w/w) and about 50% (w/w), between about 50% (w/w) and about 95% (w/w), between about 60% (w/w) and about 90% (w/w), between about 70% (w/w) and about 90% (w/w), between about 80% (w/w) and about 99% (w/w), between about 80% (w/w) and about 95% (w/w), between about 80% (w/w) and about 90% (w/w), between about 75% (w/w) and about 85% (w/w), inclusive.

The cannabinoid extract, may contain, in addition to a cannabinoid, terpenes including but are not limited to alpha bisabolol, alpha phellandrene, alpha pinene, beta caryophyllene, beta pinene, cadinene, camphene, camphor, citral, citronellol, delta 3 carene, eucalyptol, eugenol, gamma terpinene, geraniol, humulene, limonene, linalool, nerol, nerolidol, ocimene, para-cymene, phytol, pulegone, terpineol, terpinolene, valencene, or mixtures thereof.

The cannabinoid extract may be substantially free of lipids. For example, the cannabinoid extract may comprise less than about 0.1% to 1% lipids by weight.

The concentration of a terpene in the cannabinoid extract and/or the cannabinoid crystals may range between about 0% (w/w) and about 50% (w/w), between about 5% (w/w) and about 45% (w/w), between about 10% (w/w) and about 40% (w/w), between about 15% (w/w) and about 35% (w/w), or between about 20% (w/w) and about 30% (w/w), inclusive. The terpene concentration in the cannabinoid extract and/or the cannabinoid crystals also includes ranges of between about 0% (w/w) and about 5% (w/w), between about 5% (w/w) and about 10% (w/w), between about 10% (w/w) and about 15% (w/w), between about 15% (w/w) and about 20% (w/w), between about 20% (w/w) and about 25% (w/w), between about 25% (w/w) and about 30% (w/w), between about 30% (w/w), inclusive.

Anti-Solvent Temperatures

In the methods disclosed herein, the temperature of the anti-solvent, such as the temperature of the anti-solvent used to cool the cannabinoid extract and/or cannabinoid crystals, can range from about −40° C. to about 20° C., from about −30° C. to about 20° C., from about −20° C. to about 20° C., from about −10° C. to about 20° C., or from about 0° C. to about 10° C. These temperature ranges can also be expressed as from about −40° C. to about −20° C., from about −30° C. to about −20° C., from about −20° C. to about −10° C., from about −10° C. to about 0° C., from about 0° C. to about 10° C., from about 10° C. to about 20° C., from about 15° C. to about 20° C., from about 10° C. to about 15° C., or from about 4° C. to about 10° C. Thus, the temperature of the anti-solvent is about −40° C., about −35° C., about −30° C., about −25° C., about −20° C., about −15° C., about −10° C., about −5° C., about 0° C., about 5° C., about 10° C., about 15° C., about 20° C., about 5° C., about 15° C., about 4° C., about 14° C., about −5° C., or about 5° C. The anti-solvent may be pentane maintained between −20° C. to 0° C.

Pesticides and/or fungicides applied to the *Cannabis* plants and the removal of any pesticides, e.g., by rinsing or washing, determines the concentration of any pesticides/fungicides extracted by the system with the cannabinoid and terpenes. The concentration of pesticides or fungicides in the cannabinoid extract and/or cannabinoid crystals may range from about 0 ppm to about 1000 ppm, from about 0.0001 ppm to about 500 ppm, from about 0.001 ppm to about 400 ppm, from about 0.01 ppm to about 300 ppm, from about 0.1 ppm to about 200 ppm, from about 1 ppm to about 100 ppm, from about 5 ppm to about 50 ppm, or from about 10 ppm to about 25 ppm. The concentration ranges for pesticides or fungicides also include from about 0.1 ppm to about 10 ppm, from about 10 ppm to about 25 ppm, from about 25 ppm to about 50 ppm, from about 50 ppm to about 100 ppm, from about 100 ppm to about 200 ppm, from about 200 ppm to about 500 ppm, or from about 500 ppm to about 1000 ppm.

Pesticide and fungicide concentrations within these ranges include about 0 ppm, about 0.0001 ppm, about 0.001 ppm, about 0.01 ppm, about 0.1 ppm, about 1 ppm, about 5 ppm, about 10 ppm, about 25 ppm, about 50 ppm, about 100 ppm, about 200 ppm, about 500 ppm, or about 1000 ppm.

The cannabinoid extract and/or cannabinoid crystals can comprise less than 0.5%, 0.1%, 0.01%, or 0.001% w/w pesticides, fungicides, fertilizers, and mixtures thereof. For example, the cannabinoid extract and/or cannabinoid crystals can comprise a concentration of pesticides or fungicides ranging from about 0 ppm to 10 ppm.

Cannabinoid Decarboxylation

The disclosure further provides improved methods for decarboxylation and crystallization of a cannabinoid acid to form a cannabinoid. For example, cannabidiol acid (CBDA) may be decarboxylated using the methods described herein to form cannabidiol (CBD):

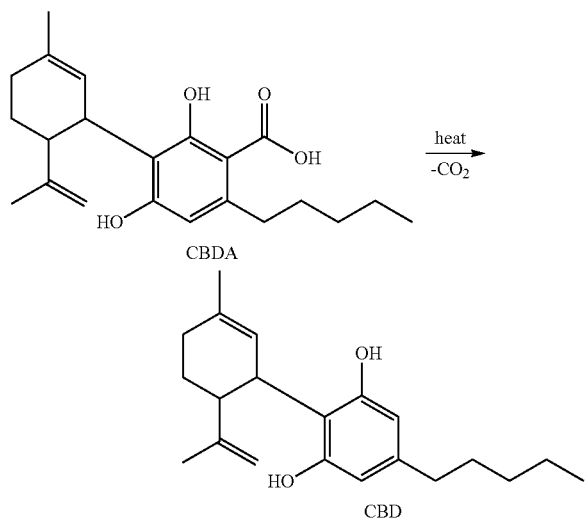

CBDA

CBD

A similar chemical reaction can be used to decarboxylate a cannabinoid acid to form the cannabinoid, the physiologically active form of the cannabinoid. For example, $\Delta^9$-tetrahydrocannabinol acid ($\Delta^9$-THCA), cannabidiol acid (CBDA), and cannabigerol acid (CBGA) may be decarboxylated to form their physiologically active neutral forms, $\Delta^9$-tetrahydrocannabinol ($\Delta^9$-THC), cannabidiol (CBD), and cannabigerol (CBG).

The current methodology for the decarboxylation (removal of —COOH species) from a cannabinoid, e.g., cannabidiol acid, to the active cannabinoid, e.g., cannabidiol (CBD), and its subsequent crystallization is time-consuming and involves the exposure to toxic, noxious hydrocarbon solvents that contaminate the crystallized product. These solvents are difficult to abate from the final crystallized product and are subject to State-mandated minimum residual requirements for the legal sale of these crystals. Further, a common method of decarboxylation and crystallization of cannabinoids involves heated vacuum crystallization which incurs high energy demands, long processing times, and up to a 60% loss, by weight, of the potential yield.

The system and methods described herein reduces the time consumed, energy costs, and improves the process of isolating a cannabinoid crystal from biomass-extracted crude cannabis extracts. Further, the methods and systems described herein may be GMP compliant, allowing the cannabinoid crystals to be used in food and pharmaceuticals.

In one embodiment, a cannabidiol acid extract is passed through a heat transfer screw conveyor for 100° C. to 130° C. for 1-30 minutes. The heat transfer screw conveyor does not allow the ventilation of the $CO_2$ produced, instead, the $CO_2$ produced from decarboxylation serves as a foaming agent to create a heated CBD foam. In another embodiment, an extraneous foaming agent may be added to the heat transfer screw. The foaming agent may be a blowing agent. The blowing agent may be carbon dioxide ($CO_2$), pentane, butane, a chlorofluorocarbon, or mixtures thereof. The heat transfer screw conveyor is coupled to a solution tube where cold pentane at about −20° C. to 0° C. is passed over the heated CBD foam. See FIG. 1. The cold pentane (at about −20° C. to 0° C.) is fed in at the proximal end where the heated cannabidiol (CBD) foam is extruded from the heat transfer screw conveyor and runs along the length of the headed CBD foam, allowing the $CO_2$ to vent and allowing the pentane to absorb terpenes. At the distal end, a cooled, CBD crystal, substantially free of terpenes and other cannabinoids is extruded. A sonication device may be arranged at the distal end to provide ultrasonic cavitation. The ultrasonic cavitation may break up the CBD crystals to further increase surface area, allowing the anti-solvent more time to extract any residual terpenes.

In one embodiment, the cannabinoid extract is passed through a heat transfer screw conveyor for 100° C. to 130° C. for 1-30 minutes. The heat transfer screw conveyor does not allow the ventilation of the $CO_2$ produced, instead, the $CO_2$ produced from decarboxylation serves as a foaming agent to create a heated cannabinoid foam. In another embodiment, an extraneous foaming agent may be added to the heat transfer screw. The foaming agent may be a blowing agent. The blowing agent may be carbon dioxide ($CO_2$), pentane, butane, a chlorofluorocarbon, or mixtures thereof. The heat transfer screw conveyor is coupled to a solution tube where cold pentane at about −20° C. to 0° C. is passed over the heated cannabinoid foam. See FIG. 1. The cold pentane (at about −20° C. to 0° C.) is fed in at the proximal end where the heated cannabinoid foam is extruded from the heat transfer screw conveyor and runs along the length of the headed cannabinoid foam, allowing the $CO_2$ to vent and allowing the pentane to absorb terpenes. At the distal end, a cooled, cannabinoid crystal, substantially free of terpenes is extruded. A sonication device may be arranged at the distal end to provide ultrasonic cavitation. The ultrasonic cavitation may break up the cannabinoid crystals to further increase surface area, allowing the anti-solvent more time to extract any residual terpenes.

Decarboxylation

Crude cannabis extract may be winterized, e.g., have the lipids removed, prior to heat treatment to decarboxylate the CBDA to form cannabidiol (CBD) using methods known in the art. The inventor unexpectedly discovered that the lipid fraction comprising gums, resins, phospholipids, and oils, primarily traps the antifungal agents, pesticides, and fertilizers. By removing the lipids prior to decarboxylation and crystallization, these noxious agents can be excluded from the final product. The lipids may be removed by membrane filtration, de-waxing, winterization, or a combination thereof.

Crystallization

The cannabinoid extract may be subjected to crystallization. The concentration of a cannabinoid in a cannabinoid crystal formed by the system and methods described herein may range between about 0% (w/w) and about 100% (w/w), between about 50% (w/w) and about 95% (w/w), between about 10% (w/w) and about 100% (w/w), between about 55% (w/w) and about 95% (w/w), or between about 20% (w/w) and about 90% (w/w). The cannabinoid in a cannabinoid crystal also includes ranges of between about 10% (w/w) and about 50% (w/w), between about 5% (w/w) and about 100% (w/w), between about 10% (w/w) and about 55% (w/w), between about 65% (w/w) and about 80% (w/w), between about 90% (w/w) and about 95% (w/w), between about 95% (w/w) and about 100% (w/w), between about 90% (w/w) and about 98% (w/w), between about 95% (w/w) and about 99% (w/w), between about 80% (w/w) and about 95% (w/w), or between about 95% (w/w) and about 99.99% (w/w).

Cannabinoids found in the cannabinoid crystal include, but are not limited to, tetrahydrocannabinol, cannabigerol, cannabinol, cannabichromene, cannabigerivarin, tetrahydrocannabivarin, cannabidivarin, cannabichromevarin, or a mixture thereof. It should be appreciated that the extract may also include cannabinoid acids, such as cannabigerolic acid, Δ9-tetrahydrocannabinolic acid, cannabidiolic acid, cannabichromenenic acid, cannabigerovarinic acid, tetrahydrocanabivarinic acid, cannabidivarinic acid, cannabichromevarinic acid, or mixtures thereof. The crystal may consist essentially of cannabidiol (CBD). For example, the cannabinoid crystal may comprise at least 90% cannabidiol, 95% cannabidiol, 98% cannabidiol, 99% cannabidiol, or 99.9% cannabidiol, optionally substantially free of tetrahydrocannabinol, optionally delta-9-tetrahydrocannabinol (delta-9 THC).

The cannabinoid crystals may be sustainably free of terpenes. For example, the cannabinoid crystals may comprise less than about 1% terpenes by weight. Terpenes include but not limited to, alpha bisabolol, alpha phellandrene, alpha pinene, beta caryophyllene, beta pinene, cadinene, camphene, camphor, citral, citronellol, delta 3 carene, eucalyptol, eugenol, gamma terpinene, geraniol, humulene, limonene, linalool, nerol, nerolidol, ocimene, para-cymene, phytol, pulegone, terpineol, terpinolene, valencene, or mixtures thereof. Further terpenes may include trans-nerolidol, terpinolene, terpineol, saniene hydrate, L-fenchone, guaiol, geraniol, γ-terpinene, β-pinene, α-terpinene, α-humulene, α-cedrene, α-Pinene, R-Limonene, S-Camphor, fenchyl alcohol, R-camphor, (−)-borneol, (+)-borneol, (+)-pulegone, valencene, transcaryophyllene, p-mentha 1,5-diene, ocimene, nerol, linalool, isoborneol, hexahydrothymol, geranyl acetate, farnesene, eucalyptol, cis-nerolidol, camphor, camphene, β-myrcene, carene, (−)-isopulegol, caryophyllene oxide, α-bisabolol, (+)-fenchone, and (+)-cedrol. For example, the cannabinoid crystal may comprise cannabidiol, and, optionally may be substantially free of THC, optionally delta-9-tetrahydrocannabinol (delta-9 THC), and terpenes.

Additionally, the cannabinoid crystals are also substantially free of cannabis flavonoids including but are not limited to quercetin, luteolin, kaempferol, cannaflavin A, and apigenin.

Frequency

The ultrasonic unit can use ultrasonic energy at about 1 to about 100 kHz. The generator should produce enough power to generate a transducer frequency sufficient to disrupt cannabinoid crystals, e.g., about 1 to about 100 kHz. For example, the ultrasonic disruption can be performed at a frequency of about 1 kHz, 2 kHz, 3 kHz, 4 kHz, 5 kHz, 6 kHz, 7 kHz, 8 kHz, 9 kHz, 10 kHz, 11 kHz, 12 kHz, 13 kHz, 14 kHz, 15 kHz, 16 kHz, 17 kHz, 18 kHz, 19 kHz, 20 kHz, 21 kHz, 22 kHz, 23 kHz, 24 kHz, 25 kHz, 26 kHz, 27 kHz, 28 kHz, 29 kHz, 30 kHz, 31 kHz, 32 kHz, 33 kHz, 34 kHz, 35 kHz, 36 kHz, 37 kHz, 38 kHz, 39 kHz, 40 kHz, 41 kHz, 42 kHz, 43 kHz, 44 kHz, 45 kHz, 46 kHz, 47 kHz, 48 kHz, 49 kHz, 50 kHz, 51 kHz, 52 kHz, 53 kHz, 54 kHz, 55 kHz, 56 kHz, 57 kHz, 58 kHz, 59 kHz, 60 kHz, 61 kHz, 62 kHz, 63 kHz, 64 kHz, 65 kHz, 66 kHz, 67 kHz, 68 kHz, 69 kHz, 70 kHz, 71 kHz, 72 kHz, 73 kHz, 74 kHz, 75 kHz, 76 kHz, 77 kHz, 78 kHz, 79 kHz, 80 kHz, 81 kHz, 82 kHz, 83 kHz, 84 kHz, 85 kHz, 86 kHz, 87 kHz, 88 kHz, 89 kHz, 90 kHz, 91 kHz, 92 kHz, 93 kHz, 94 kHz, 95 kHz, 96 kHz, 97 kHz, 98 kHz, 99 kHz, or about 100 kHz. The ultrasonic disruption can be at a frequency of about 20 to about 50 kHz, about 10 to about 100 kHz, about 30 to about 70 kHz, about 1 to about 10 kHz, about 280 to about 40 kHz, about 21 to about 450 kHz, about 26 to about 380 kHz, about 29 to about 39 kHz, about 32 to about 36 kHz, about 34 to about 38 kHz, about 25 to about 40 kHz, about 30 to about 40 kHz, about 10 to about 40 kHz, about 30 to about 45 kHz, about 25 to about 50 kHz, about 31 to about 39 kHz, or about 32 to about 42 kHz. The ultrasonic treatment can be at a frequency of about 35 kHz. In an embodiment, the cannabinoid crystal is a cannabidiol crystal, optionally substantially free of THC, optionally delta-9-tetrahydrocannabinol (delta-9 THC).

Time

The cannabinoid crystal product may undergo ultrasonic cavitation, where ultrasonic cavitation is applied for any suitable amount of time as to disrupt the cannabinoid crystal product, breaking it into pieces, e.g., from about 1 second to about 60 seconds. The cannabinoid crystal product can undergo ultrasonic treatment, where ultrasonic cavitation is applied for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 seconds. The cannabinoid crystal product can be exposed to ultrasonic energy, where ultrasonic cavitation is applied for 1-50 seconds, 5-50 seconds, 10-50 seconds, 25-35 seconds, 21-45 seconds, 25-40 seconds, 30-40 seconds, 27-45 seconds, 29-39 seconds, 21-31 seconds, 23-32 seconds, 29-38 seconds, or 24-36 seconds. In an embodiment, the cannabinoid crystal is a cannabidiol crystal, optionally substantially free of THC, optionally delta-9-tetrahydrocannabinol (delta-9 THC).

The ultrasonic cavitation may be applied in pulses. The ultrasonic cavitation may be pulsed, i.e., applied via a mixture of on and off cycles. The ultrasonic cavitation pulsing "on/off" cycle may be applied for 5 seconds, then off for 5 seconds, and repeated for a total of 30 to 240 seconds. The ultrasonic cavitation may be applied for 5 seconds on/5 seconds off, 10 seconds on/10 seconds off, 15 seconds on/15 seconds off, 20 seconds on/20 seconds off, 25 seconds on/25 seconds off, 30 seconds on/30 seconds off, 35 seconds on/35 seconds off, 40 seconds on/40 seconds off, 45 seconds on/45 seconds off, or 50 seconds on/50 seconds off. The ultrasonic cavitation may be applied for 5 seconds on/10 seconds off, 10 seconds on/20 seconds off, 25 seconds on/15 seconds off, 20 seconds on/40 seconds off, 35 seconds on/25 seconds off, 35 seconds on/30 seconds off, 135 seconds on/35 seconds off, 120 seconds on/30 seconds off, 60 seconds on/120 seconds off, or 100 seconds on/50 seconds off.

For example, the ultrasonic cavitation may be applied for 5 seconds, then off for 5 seconds, and repeated for a total of 30 to 180 seconds. The ultrasonic cavitation may be an equal set of "on/off" pulses, for example, 5 seconds on/5 seconds off, 10 seconds on/10 seconds off, 15 seconds on/15 seconds off, 20 seconds on/20 seconds off, 25 seconds on/25 seconds off, 30 seconds on/30 seconds off, 35 seconds on/35 seconds off, 40 seconds on/40 seconds off, 45 seconds on/45 seconds off, or 50 seconds on/50 seconds off. In another embodiment, the ultrasonic cavitation may be an unequal set of "on/off" pulses, for example, 5 seconds on/10 seconds off, 10 seconds on/20 seconds off, 25 seconds on/15 seconds off, 20 seconds on/40 seconds off, 35 seconds on/25 seconds off, 35 seconds on/30 seconds off, 135 seconds on/35 seconds off, 120 seconds on/30 seconds off, 60 seconds on/120 seconds off, or 100 seconds on/50 seconds off.

Power

Any high-power ultrasonic device can be used in the methods and systems described herein. Power requirements are a function of the amount of cannabinoid crystal being subjected to ultrasonic cavitation. The power range can be expressed in terms of kilowatts of ultrasonic energy per kilogram of cannabinoid crystal product, for example the ultrasonic cavitation can be applied at a power of from about 0.1 to about 1,000 kW/kg of cannabinoid crystal product by weight, which is an amount of power sufficient to disrupt the cannabinoid crystal product. For example, the ultrasonic cavitation can be applied at a power of about 0.1, 0.2, 0.3, 0.4, 0.5, 0.6, 0.7, 0.8, 0.9, or about 1 kW/kg of cannabinoid crystal product by weight. The ultrasonic cavitation can be applied at a power of about 0.1 to about 0.9 kW/kg of cannabinoid crystal product by weight, about 0.5 to about 1.0 kW/kg of cannabinoid crystal product by weight, about 0.25 to about 0.75 kW/kg of cannabinoid crystal product by weight, about 0.3 to about 0.6 kW/kg of cannabinoid crystal product by weight, about 0.2 to about 0.8 kW/kg of cannabinoid crystal product by weight, or about 0.15 to about 0.95 kW/kg of cannabinoid crystal product by weight. In an embodiment, the cannabinoid crystal comprises cannabidiol, substantially free of THC.

Filtration Capture of Cannabinoid Crystals

The cannabinoid crystals may be filtered through a filter, mesh, screen, or membrane to produce a permeate and a retentate. The permeate comprises the solvent. The retentate comprises the cannabinoid crystals. Suitable membranes have a pore diameter of about 1-100 µm. Suitable membranes for use in the disclosed methods include: Synder NFG, Synder XT, Synder MT, and Synder VT produced by Synder Filtration, Inc. (Vacaville, Calif.); GE Osmonics UF GK, GE Osmonics UF GH, GE Osmonics UF PT, and GE Osmonics UF GE available from SterlitechCorporation (Kent, Wash.); TriSep OF UA60, TriSep NF XN45, and TriSep NF TS40 produced by TriSep Corporation (Goleta, Calif.); and Dow Filmtec NF produced by Dow Chemical Company (Midland, Mich.). Organic solvent stable filters, such as SolSep UF10706, SolSep UF03705, and SolSep NF080105 produced by SolSep BV (St. Eustatius, Netherlands); and Novamem PVDF20 and Novamem PEEK 1000 produced by Novamen Ltd. (Schlieren, Switzerland) may be used.

The pressure of the solvent at the membrane may range from about 50 pound-force per square inch (psi) to about 600 psi, about 75 psi to about 500 psi, about 100 psi to about 400 psi, about 125 psi to about 300 psi, or about 150 psi to about 250 psi. Suitable operating pressure ranges can also be expressed as about 50 psi to about 100 psi, from about 100 psi to about 150 psi, from about 150 psi to about 200 psi, from about 200 psi to about 250 psi, from about 250 psi to about 300 psi, from about 300 psi to about 350 psi, from about 350 psi to about 400 psi, from about 400 psi to about 450 psi, from about 450 psi to about 500 psi, from about 500 psi to about 550 psi, or from about 550 psi to about 600 psi. Contemplated solvent pressures also include about 50 psi, about 100 psi, about 150 psi, about 175 psi, about 200 psi, about 225 psi, about 250 psi, about 300 psi, about 350 psi, about 400 psi, 450 psi, about 500 psi, about 550 psi, or about 600 psi.

The volumetric flow rate (Q) of the solvent depends on the surface are of the membrane. For example, the volumetric flow rate of the solvent may be from about 0 L/h to about 1000 L/h, from about 10 L/h to about 750 L/h, from about 20 L/h to about 500 L/h, from about 30 L/h to about 450 L/h, from about 40 L/h to about 400 L/h, from about 50 L/h to about 350 L/h, from about 75 L/h to about 300 L/h, from about 100 L/h to about 250 L/h. In full scale processes in which the surface area of the membrane is greater than about 25 $m^2$, the volumetric flow rate of the solvent may exceed 1000 L/h. The volumetric flow rate of the solvent may also range from about 0 L/h to about 10 L/h, from about 10 L/h to about 50 L/h, from about 50 L/h to about 100 L/h, from about 100 L/h to about 200 L/h, from about 200 L/h to about 400 L/h, from about 400 L/h to about 600 L/h, from about 600 L/h to about 800 L/h, from about 800 L/h to about 1000 L/h. Solvent volumetric flow rates include about 5 L/h, about 10 L/h, about 15 L/h, about 20 L/h, about 25 L/h, about 50 L/h, about 75 L/h, about 100 L/h, about 125 L/h, about 150 L/h, about 175 L/h, about 200 L/h, about 250 L/h, about 400 L/h, about 600 L/h, about 800 L/h, about 1000 L/h.

The temperature of the permeate ranges from about 0° C. to about 50° C., from about 0° C. to about 40° C., from about 0° C. to about 30° C., from about 10° C. to about 20° C., or from about 0° C. to about 10° C. Suitable temperature ranges also include about 0° C. to about 30° C., from about 0° C. to about −20° C., from about 0° C. to about 10° C., from about 10° C. to about 20° C., from about 0° C. to about 10° C., from about 10° C. to about 20° C., from about 20° C. to about 30° C., from about 30° C. to about 40° C., or from about 40° C. to about 50° C. Temperatures within these ranges include about 0° C., about 5° C., about 10° C., about 15° C., about 20° C., about 25° C., about 30° C., about 35° C., about 40° C., about 45° C., or about 50° C.

The disclosed methods employ pressures of the permeate including ranges from about 50 pound-force per square inch (psi) to about 600 psi, about 75 psi to about 500 psi, about 100 psi to about 400 psi, about 125 psi to about 300 psi, or about 150 psi to about 250 psi. Other contemplated pressure ranges include about 50 psi to about 100 psi, from about 100 psi to about 150 psi, from about 150 psi to about 200 psi, from about 200 psi to about 250 psi, from about 250 psi to about 300 psi, from about 300 psi to about 350 psi, from about 350 psi to about 400 psi, from about 400 psi to about 450 psi, from about 450 psi to about 500 psi, from about 500 psi to about 550 psi, or from about 550 psi to about 600 psi. Pressures falling within these ranges include about 50 psi, about 100 psi, about 150 psi, about 175 psi, about 200 psi, about 225 psi, about 250 psi, about 300 psi, about 350 psi, about 400 psi, 450 psi, about 500 psi, about 550 psi, or about 600 psi.

The flow rate of the permeate may be 0-1,000 liters per hour. Because the flow rate is proportional to the surface area of the membrane, the flow rate of the permeate may scale much higher. In other words, the flux of the permeate through the membrane ranges from about 0 $L/h \cdot m^2$ to about 1000 $L/h \cdot m^2$, from about 10 $L/h \cdot m^2$ to about 750 $L/h \cdot m^2$, from about 20 $L/h \cdot m^2$ to about 500 $L/h \cdot m^2$, from about 30 $L/h \cdot m^2$ to about 450 $L/h \cdot m^2$, from about 40 $L/h \cdot m^2$ to about 400 $L/h \cdot m^2$, from about 50 $L/h \cdot m^2$ to about 350 $L/h \cdot m^2$, from about 75 $L/h \cdot m^2$ to about 300 $L/h \cdot m^2$, from about 100 $L/h \cdot m^2$ to about 250 $L/h \cdot m^2$. The flux of the permeate through the membrane may also range from about 0 $L/h \cdot m^2$ to about 10 L/h·m², from about 10 L/h·m² to about 50 L/h·m², from about 50 L/h·m² to about 100 L/h·m², from about 100 L/h·m² to about 200 L/h·m², from about 200 L/h·m² to about 400 L/h·m², from about 400 L/h·m² to about 600 L/h·m², from about 600 L/h·m² to about 800 L/h·m², from about 800 L/h·m² to about 1000 L/h·m². Particular fluxes within such ranges include about 5 L/h·m², about 10 L/h·m², about 15 L/h·m², about 20 L/h·m², about 25 L/h·m², about 50 L/h·m², about 75 L/h·m², about 100 L/h·m², about 125 L/h·m², about 150 L/h·m², about 175 L/h·m², about 200 L/h·m², about 250 L/h·m², about 400 L/h·m², about 600 L/h·m², about 800 L/h·m², about 1000 L/h·m².

Cannabinoid Acid Decarboxylation and Crystallization

The disclosure generally relates to improved methods for decarboxylation of cannabinoid extracts that may be heat treated to decarboxylate a cannabinoid acid to produce a cannabinoid. The resultant heat-treated cannabinoid extract is then subjected to crystallization in a tank of solvent, and, optionally, a nucleating agent or anti-solvent are added to assist in crystallization. The cannabinoid crystals produced by decarboxylation and crystallization are collected, tested, weighed, and packaged, preferably in nitrogen-flushed, light proof containers (e.g., vials or bags).

In another example, a cannabinoid extract is heat treated to decarboxylate cannabidiol acid (CBDA) to produce cannabidiol (CBD) by placing a thin layer of the cannabinoid extract on a heated plate or passing the cannabinoid extract through a heat transfer screw conveyor. The heat transfer screw conveyor may be fed into a crystallization vessel containing a pentane solvent maintained at a temperature between −20° C. and 0° C. Optionally, a nucleating agent or anti-solvent can be added to aid crystallization. In one embodiment, the cannabinoid extract is passed through a heat transfer screw conveyor for 100° C. to 130° C. for 1-30 minutes. The heat transfer screw conveyor does not allow the ventilation of the CO produced, instead, the $CO_2$ produced from decarboxylation serves as a foaming agent to create a heated CBD foam. The heat transfer screw conveyor is coupled to a solution tube where cold pentane at about −20° C. to 0° C. is passed over the heated CBD foam. See FIG. 1A. The cold pentane (at about −20° C. to 0° C.) is fed in at the proximal end where the heated CBD foam is extruded from the heat transfer screw conveyor and runs along the length of the headed CBD foam, allowing the $CO_2$ to vent and absorbing terpenes and cannabinoids. At the distal end, a cooled, CBD crystal, substantially free of terpenes and other cannabinoids is extruded.

The cannabinoid crystals produced by decarboxylation and crystallization are collected by filtration and the solvent(s) may be subjected to membrane exchange to separate the solvent(s). In another embodiment, the cannabinoid crystals may be washed with additional solvent and dried. The cannabinoid crystals collected may be tested, weighed, and packaged, preferably in nitrogen-flushed, light proof containers (e.g., vials, jars, bags).

Decarboxylation

Crude cannabis extract may be winterized (have the lipids removed) removed prior to heat treatment to decarboxylate the cannabinoid acid to a form cannabinoid. The inventor found that the lipid fraction comprising gums, resins, phospholipids, and oils, primarily traps the antifungal agents, pesticides, and fertilizers. By removing the lipids prior to decarboxylation and crystallization, these noxious agents can be excluded from the final product. The lipids may be removed by membrane filtration, de-waxing, winterization, or a combination thereof.

The decarboxylation system and methods described herein utilize a large surface area-heated platform that facilitates a time-expedient decarboxylation of the cannabinoid isolate. Preferably, the cannabinoid extract is spread thinly (e.g., less than 1 cm) over a large-surface area-heated platform. The decarboxylated product is then moved into a drain that is slightly uphill of the heated plate. This drain feeds the product into the crystallization vessel where the cannabinoid is crystallization and recovered by membrane filtration. The solvents used in the crystallization process may be filtered by membrane filtration and recovered for further use. The starting material may be a miscella comprising lipids and cannabinoids, or a more refined cannabis extract consisting substantially of cannabidiol acid.

In another embodiment, the decarboxylation system and methods described herein utilize a heat transfer screw conveyor that provides a time-expedient decarboxylation of a cannabinoid extract comprising a cannabinoid acid. Preferably, the cannabinoid extract is into the screw conveyor and heated to between 110° C. to 130° C. for a dwell time of between 1-60 minutes. The decarboxylated product is feed into a crystallization vessel where the cannabinoid is crystallized and recovered by membrane filtration. The cannabinoid crystallization may be aided by the addition of an anti-solvent or nucleating agent (e.g., chitosan). The solvents used in the crystallization process may be filtered by membrane filtration and recovered for further use. The starting material may be a miscella comprising lipids and cannabinoids, or a more refined cannabis extract consisting substantially of cannabidiol acid.

The decarboxylation system and methods described herein utilize a large surface area-heated platform that facilitates a time-expedient decarboxylation cannabis extract. The cannabinoid extract is first spread thinly (e.g., less than 1 cm) over a large-surface area-heated platform that is inclined, the platform having a drain located at or near the top of the incline. The decarboxylated product is formed over time and is then moved into the drain. The drain feeds the product into a crystallization vessel, where the cannabinoid is crystallized and recovered by membrane filtration. The solvents used in the crystallization process can be filtered by membrane filtration and recovered for further use. The starting material cannabis extract can be a miscella comprising lipids and cannabinoids, or a more refined cannabis extract consisting essentially of cannabinoid.

The crude cannabis extract comprising a cannabinoid acid may be applied to substantially flat surface and heating to about 110° C. to 130° C. for 1-60 minutes. The crude cannabis extract may be applied to the substantially flat surface in a thin layer. For example, less than 1-10 cm in thickness, preferably less than 1-3 cm in thickness. The heating decarboxylate the cannabinoid acid to form a cannabinoid. The heat-treated cannabis extract comprising a cannabinoid is then moved by scraping means off the substantially flat surface into a crystallization vessel. The scraping may be accomplished by automated or manual blade(s). The surface may made of food-grade stainless steel, PTFE (TEFLON®). The scrapers may be blades, brushes, or combs configured to move the heated cannabis extract into a crystallization vessel. The scraper may be made of silicon or another heat-resistant food-grade polymer. In one embodiment, the cannabis extract may be applied in a thin layer, heated, and moved over the edge of an elevated surface into the crystallization vessel. In another embodiment, the surface is a drum, optionally cylindrical or conical in shape, where a nozzle applies the cannabis extract to the heat surface in a thin layer, and is followed by a scraper (e.g., 1-60 minute delay to allow for heating), that moves the heated cannabis extract into a crystallization vessel. Where the surface is a drum, optionally cylindrical or conical in shape, the heated product may be moved through an opening or over an edge of the drum into a crystallization vessel. In another embodiment, the decarboxylation may occur in a heat transfer screw conveyor. The inventor unexpectedly found that minimizing steps and solvents allows for a far higher yield with great purity.

Crystallization

The cannabis extract comprising a cannabinoid is subjected to solubilization in a crystallization vessel. A solvent is added. Organic solvents including but not limited to pentane and hexane.

Suitable solvents that can be used to for crystallization include organic solvents, water (e.g., potable water), and combinations thereof. Organic solvents include alcohols, ethers, esters, ketones, alkanes, and combinations thereof. Examples of alcohols include methanol, ethanol, n-propanol, 1-propanol, n-butanol, sec-butanol, t-butanol, 1-pentanol, amyl alcohol, isoamyl alcohol, 1-hexanol, 2-hexanol, 3-hexanol, 1-heptanol, 2-heptanol, 3-heptanol, 4-heptanol, 1-octanol, 2-octanol, 1-nonanol, 1-decanol, or a mixture thereof. For example, the alcohol can be methanol, ethanol, pentane, hexane, or a mixture thereof. The solvent can be ethanol (e.g., as the sole solvent). The solvent can be pentane (e.g., as the sole solvent). The solvent can also comprise water. Examples of ethers include diethyl ether, dipropyl ether, tetrahydrofuran, and the like and combinations thereof. Examples of esters include ethyl acetate and the like. Examples of ketones include acetone, methyl ethyl ketone, and the like and combinations thereof. Examples of alkanes include pentane, hexane, heptane, and the like and combinations thereof.

Suitable solvents can be substantially free of detergents, emulsifiers, solubilizers, other organic solvents, or any combination thereof.

In some embodiments, a second solvent is added to the first solvent that acts as an anti-solvent to the first solvent, in an amount between about 1:1 and 1:5 first solvent to second solvent.

For example, a second solvent (that acts as an anti-solvent) and is added over 1-30 minutes at a ratio of about between 1:1 and 1:5 cannabis extract to the first solvent. A preferred ratio is about 1:1 cannabis extract to solvent. Once the cannabis extract is solubilized, a food-grade nucleating agent and second solvent are added to the solution that acts as an anti-solvent to the cannabinoid. The addition of this nucleating agent along with the anti-solvent may facilitate the precipitation of cannabinoid crystals out of solution. Preferred nucleating agents are polysaccharides, including but not limited to plant polysaccharides and chitosan. Preferred second solvents include water and acetonitrile.

The disclosure provides methods of preparing cannabinoid extracts that advantageously increase cannabinoid yields and decrease process time from hours to minutes. The systems and methods disclosed herein scale more easily than distillation-based methods and can be used in both batch and continuous processes. The solvent recovery methods of the disclosure are also safer than distillation, have fewer moving parts, and reduce refrigeration and heating duties. Additionally, the inventive subject matter advantageously increases yields from industrial hemp without the need to increase cannabinoid production by the hemp plants using genetic techniques. The inventors have discovered that high yields of cannabidiol can be obtained using the system and methods described herein.

The concentration of cannabinoid in a cannabinoid crystal formed by the system and methods described herein may range between about 0% (w/w) and about 100% (w/w), between about 50% (w/w) and about 95% (w/w), between about 10% (w/w) and about 100% (w/w), between about 55% (w/w) and about 95% (w/w), or between about 20% (w/w) and about 90% (w/w). The cannabinoid in a cannabinoid crystal also includes ranges of between about 10% (w/w) and about 50% (w/w), between about 5% (w/w) and about 100% (w/w), between about 10% (w/w) and about 55% (w/w), between about 65% (w/w) and about 80% (w/w), between about 90% (w/w) and about 95% (w/w), between about 95% (w/w) and about 100% (w/w), between about 90% (w/w) and about 98% (w/w), between about 95% (w/w) and about 99% (w/w), between about 80% (w/w) and about 95% (w/w), or between about 95% (w/w) and about 99.99% (w/w).

Exemplary cannabinoids in the cannabis extract include, but are not limited to tetrahydrocannabinol, cannabidiol, cannabigerol, cannabinol, cannabichromene, cannabigerivarin, tetrahydrocannabivarin, cannabidivarin, cannabichromevarin, or a mixture thereof. It should be appreciated that the extract may also include cannabinoid acids, such as cannabigerolic acid, Δ9-tetrahydrocannabinolic acid, cannabidiolic acid, cannabichromenenic acid, cannabigerovarinic acid, tetrahydrocanabivarinic acid, cannabidivarinic acid, and/or cannabichromevarinic acid. The crystal may consist essentially of cannabidiol.

The cannabinoid crystals may be sustainably free of terpenes. Terpenes include but not limited to, alpha bisabolol, alpha phellandrene, alpha pinene, beta caryophyllene, beta pinene, cadinene, camphene, camphor, citral, citronellol, delta 3 carene, eucalyptol, eugenol, gamma terpinene, geraniol, humulene, limonene, linalool, nerol, nerolidol, ocimene, para-cymene, phytol, pulegone, terpineol, terpinolene, valencene, or mixtures thereof. Further terpenes may include trans-nerolidol, terpinolene, terpineol, saniene hydrate, L-fenchone, guaiol, geraniol, γ-terpinene, β-pinene, α-terpinene, α-humulene, α-cedrene, α-Pinene, R-Limonene, S-Camphor, fenchyl alcohol, R-camphor, (−)-borneol, (+)-borneol, (+)-pulegone, valencene, transcaryophyllene, p-mentha 1,5-diene, ocimene, nerol, linalool, isoborneol, hexahydrothymol, geranyl acetate, farnesene, eucalyptol, cis-nerolidol, camphor, camphene, β-myrcene, carene, (−)-isopulegol, caryophyllene oxide, α-bisabolol, (+)-fenchone, and (+)-cedrol.

Additionally, the cannabinoid crystals are also substantially free of cannabis flavonoids including but are not limited to quercetin, luteolin, kaempferol, cannaflavin A, and apigenin.

Filtration Capture of Cannabinoid Crystals

The solvent/cannabinoid crystal slurry may be filtered through a filter, mesh, screen, or membrane to produce a first permeate and a first retentate. The first permeate comprises the first and second solvent. The first retentate comprises the cannabinoid crystals. Suitable filters have a pore diameter of about 0.1-100 μm. For example the filter may have a pore diameter of about 2 to 10 μm, 1 to 5 μm, 1 to 10 μm, 5 to 20 μm, 10 to 40 μm, or 1 to 50 μm. For example, the filter may have a pore diameter of about 1, 2, 3, 4, 5, 6, 7, 8, 9, or 10 μm.

Suitable membranes for use in the disclosed methods include: Synder NFG, Synder XT, Synder MT, and Synder VT produced by Synder Filtration, Inc. (Vacaville, Calif.); GE Osmonics UF GK, GE Osmonics UF GH, GE Osmonics UF PT, and GE Osmonics UF GE available from SterlitechCorporation (Kent, Wash.); TriSep OF UA60, TriSep NF XN45, and TriSep NF TS40 produced by TriSep Corporation (Goleta, Calif.); and Dow Filmtec NF produced by Dow Chemical Company (Midland, Mich.). Organic solvent stable filters, such as SolSep UF10706, SolSep UF03705, and SolSep NF080105 produced by SolSep BV (St. Eustatius, Netherlands); and Novamem PVDF20 and Novamem PEEK 1000 produced by Novamen Ltd. (Schlieren, Switzerland) may be used.

In the methods disclosed herein, the temperature inside the crystallization vessel from about 0° C. to about 50° C., from about 0° C. to about 40° C., from about 10° C. to about 30° C., from about 10° C. to about 20° C., or from about 0° C. to about 10° C. These temperature ranges can also be expressed as from about 0° C., from about 0° C. to about 10° C., from about 10° C. to about 20° C., from about 20° C. to about 30° C., from about 30° C. to about 40° C., or from about 40° C. to about 50° C. Thus, the temperature of the solvents in the crystallization vessel is about 0° C., about 5° C., about 10° C., about 15° C., about 20° C., about 25° C., about 30° C., about 35° C., about 40° C., about 45° C., or about 50° C. The temperature of the crystallization vessel may be maintained by means of thermal control, cooling, thermal monitoring, and insulation.

The crystal cannabinoid product may be recovered from this filteration step and may be washed with additional anti-solvent, preferably water, for purification purposes.

First and Second Solvent Separation

In embodiments where a first and second solvent (anti-solvent) are used, the first permeate is filtered through a membrane to produce a second permeate and a second retentate by means of a suitable nanofiltration membrane. The second solvent, e.g., water, is recovered as the second permeate and may optionally be recycled and/or stored for further use. The second solvent, e.g., acetylnitrile is concentrated in the second retentate, which may optionally be recycled and/or stored for further use. This membrane allows for the passage of one solvent through its media while rejecting the other solvent. This effort produces two separate solvent streams which are then appropriately prepared for further use.

Exemplary membranes include water compatible polyamide thin film composite membranes and have a molecular weight cutoff from about 10 Da to about 500 Da, from about 25 Da to about 400 Da, or from about 50 Da to about 300 Da. In some embodiments, the membrane has a molecular weight cutoff from about 50 Da to about 100 Da, from about 100 Da to about 150 Da, from about 150 Da to about 200 Da, from about 200 Da to about 250 Da, or from about 250 Da to about 300 Da. In other embodiments, the membrane has a molecular weight cutoff of about 50 Da, about 100 Da, about 150 Da, about 200 Da, about 250 Da, or about 300 Da.

For example, contemplated membranes include Synder NFG, Synder XT, and Synder NFX produced by Synder Filtration, Inc. (Vacaville, Calif.); GE Osmonics UF GE, GE Osmonics UF Duracid, and GE Osmonics UF DK available from Sterlitech Corporation (Kent, Wash.); TriSep NF TS80 and TriSep NF XN45 produced by TriSep Corporation (Goleta, Calif.); Dow Filmtec NF produced by Dow Chemical Company (Midland, Mich.); and Nanostone NF NF4 and Nanostone NF NF8 produced by Nanostone Water Inc. (Eden Prairie, Minn.). Surprisingly, such membranes maintained their integrity when used to with ethanol and methanol without dilution with water. Although use of solvent stable membranes in the disclosed methods is not preferred, use of organic solvent stable membranes is not excluded. Suitable organic solvent stable membranes include, SolSep NF090801, SolSep NF03705, SolSep SR1 NF080105, SolSep UF10706, SolSep UF03705, SolSep NF08105, and SolSep NF10706 produced by SolSep BV (St. Eustatius, Netherlands); and Novamem PVDF20 and Novamem PEEK 1000 produced by Novamen Ltd. (Schlieren, Switzerland).

The temperature of the second permeate and/or retentate may range from about 0° C. to about 50° C., from about 0° C. to about 40° C., from about 0° C. to about 30° C., from about 0° C. to about 20° C., or from about 0° C. to about 10° C. Suitable temperature ranges of the second permeate and/or retentate also include from about temperatures within these ranges include about 0° C., about 5° C., about 10° C., about 15° C., about 20° C., about 25° C., about 30° C., about 35° C., about 40° C., about 45° C., or about 50° C.

The pressure of the second permeate and/or retentate may range from about 0 pound-force per square inch (psi) to about 400 psi, from about 100 psi to about 350 psi, from about 150 psi to about 300 psi, or from about 200 psi to about 250 psi. The pressure of the second permeate and/or retentate may also range between about 0 pound-force per square inch (psi) to about 100 psi, about 100 psi to about 150 psi, about 150 psi to about 200 psi, about 200 psi to about 250 psi, about 250 psi to about 300 psi, about 300 psi to about 350 psi, or about 350 psi to about 400 psi. Pressures may also be about 14 pound-force per square inch (psi), about 100 psi, about 150 psi, about 200 psi, about 250 psi, 300 psi, about 350 psi, or about 400 psi.

Contemplated fluxes of the second permeate through the second membrane range from about 0 L/h·m$^2$ to about 1000 L/h·m$^2$, from about 10 L/h·m$^2$ to about 750 L/h·m$^2$, from about 20 L/h·m$^2$ to about 500 L/h·m$^2$, from about 30 L/h·m$^2$ to about 450 L/h·m$^2$, from about 40 L/h·m$^2$ to about 400 L/h·m$^2$, from about 50 L/h·m$^2$ to about 350 L/h·m$^2$, from about 75 L/h·m$^2$ to about 300 L/h·m$^2$, from about 100 L/h·m$^2$ to about 250 L/h·m$^2$. Other suitable fluxes of the second permeate through the second membrane include ranges from about 0 L/h·m$^2$ to about 10 L/h·m$^2$, from about 10 L/h·m$^2$ to about 50 L/h·m$^2$, from about 50 L/h·m$^2$ to about 100 L/h·m$^2$, from about 100 L/h·m$^2$ to about 200 L/h·m$^2$, from about 200 L/h·m$^2$ to about 400 L/h·m$^2$, from about 400 L/h·m$^2$ to about 600 L/h·m$^2$, from about 600 L/h·m$^2$ to about 800 L/h·m$^2$, from about 800 L/h·m$^2$ to about 1000 L/h·m$^2$. Thus, the flux of the second permeate through the second membrane may be about 5 L/h·m$^2$, about 10 L/h·m$^2$, about 15 L/h·m$^2$, about 20 L/h·m$^2$, about 25 L/h·m$^2$, about 50 L/h·m$^2$, about 75 L/h·m$^2$, about 100 L/h·m$^2$, about 125 L/h·m$^2$, about 150 L/h·m$^2$, about 175 L/h·m$^2$, about 200 L/h·m$^2$, about 250 L/h·m$^2$, about 400 L/h·m$^2$, about 600 L/h·m$^2$, about 800 L/h·m$^2$, about 1000 L/h·m$^2$. These fluxes correspond to flow rates of 0-600 liters per hour, or higher depending on the scale of the process (e.g., membrane surface area).

Decarboxylation

Crude cannabis extract can be defatted to have the lipids removed prior to heat treatment to decarboxylate the cannabinoid acid to form a cannabinoid, since the lipid fraction comprising gums, resins, phospholipids, and oils, primarily traps the antifungal agents, pesticides, and fertilizers. By removing the lipids prior to decarboxylation and crystallization, these agents can be excluded from the final product. The lipids can be removed by membrane filtration, de-waxing, winterization, or a combination thereof.

The crude cannabis extract comprising a cannabinoid can be applied to a substantially flat surface and heating to about 110° C. to about 130° C. for about 1 minute to about 60 minutes. The crude cannabis extract can be applied to a heated, inclined, and substantially flat surface in a thin layer. For example, less than 1-10 cm in thickness, preferably less than 1-3 cm in thickness. The heating decarboxylates a cannabinoid acid to form a cannabinoid. The heat-treated cannabis extract comprising cannabinoid is then moved in any suitable fashion, e.g., by scraping using a scraper, off the heated, inclined, and substantially flat surface into a crystallization vessel. The moving can be accomplished in an automated or manual fashion. The heated, inclined, and substantially flat surface can be made from any suitable material, including food-grade stainless steel, PTFE (TEFLON®), ceramic or the like. Suitable scrapers include blades, brushes, or combs configured to move the heated cannabis extract into a crystallization vessel. The scraper can be made of any suitable material, such as silicon or another heat-resistant food-grade polymer. The cannabis extract can be applied in a thin layer, heated, and moved over the edge of the inclined surface into the crystallization vessel. Alternatively, the substantially flat surface can be a drum, optionally cylindrical or conical in shape, where a nozzle applies the cannabis extract to the heat surface in a thin layer, and is followed by a scraper (e.g., 1-60 minute delay to allow for heating), that moves the heated cannabis extract into a crystallization vessel. Where the surface is a drum, optionally cylindrical or conical in shape, the heated product can be moved through an opening or over an edge of the drum into a crystallization vessel. It has been unexpectedly found that minimizing steps and solvents allows for a far higher yield with great purity of a cannabinoid.

Cannabinoid Composition Pellets

A method for pelletizing a cannabinoid composition comprising admixing a cannabinoid composition and a binding agent to form a cannabinoid-binding agent mixture.

The binding agent may be a food-grade binding agent. The binding agent may be a polysaccharide, gums, protein, or combination thereof. The binding agent may be methyl cellulose. The binding agent may be soy powder, rice, xanthan gum, agar, *psyllium* husk, flax meal, chia seed, nut butters, seed butters, gluten, tapioca, corn starch, potato starch, flour, aliginate, carrageenan, carboxymethy cellulose, methyl cellulose, tragacanth, guar gum, sodium pectate, pectin, gum tragacanth, or a mixture thereof. The flour may be Teff flour, buckwheat flour, Amaranth flour, chickpea flour, sorghum flour, almond flour, rice flower, or a combination thereof.

The method may comprise admixing the cannabinoid and a binding agent in a mixer, blender, kneader, roll mill, or extruder.

The cannabinoid-binding agent mixture may be formed into pellets. The cannabinoid-binding agent mixture may be extruded into pellets. The cannabinoid-binding agent mixture may be pelletized by casting means.

The cannabinoid and binding agent may be mixed at a temperature between about 60° C. and 200° C.

The cannabinoid and binding agent may be mixed for between about 1 minute and 180 minutes. The cannabinoid and binding agent may be mixed for between about 1-10 minutes, 1-20 minutes, 5-10 minutes, 15-30 minutes, 20-40 minutes, 30-60 minutes, 1-30 minutes, 1-60 minutes, 1-80 minutes, 1-100 minutes, or 1-120 minutes.

The cannabinoid-binding agent mixture may be cooled to a temperature of about −20° C. to 20° C. The temperature may be between about −20° C. to 10° C., −20° C. to 0° C., −10° C. to 10° C., 0° C. to 20° C., or 0° C. to 5° C. The temperature may be about −20° C., −19° C., −18° C., −17° C., 16° C., −15° C., −14° C., −13° C., −12° C., −11° C., −10° C., −9° C., −8° C., −7° C., −6° C., −5° C., −4° C., −3° C., −2° C., −1° C., 0° C., 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., or 20° C.

The concentration of the cannabinoid in the cannabinoid-binding agent mixture may be between about 50% (w/w) and about 100% (w/w), between about 85% (w/w) and about 95% (w/w), between about 80% (w/w) and about 90% (w/w), between about 85% (w/w) and about 95% (w/w), or between about 98% (w/w) and about 100% (w/w), inclusive.

The concentration of the binding agent in the cannabinoid-binding agent mixture may be between about 0.1% (w/w) and about 50% (w/w), between about 5% (w/w) and about 45% (w/w), between about 10% (w/w) and about 30% (w/w), between about 25% (w/w) and about 35% (w/w), or between about 8% (w/w) and about 10% (w/w), inclusive.

The cannabinoid composition and binding agent may be mixed at a ratio between about 1:1 to 20:1 by weight. The ratio is about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1.

The cannabinoid composition may comprise a cannabinoid, terpene, lipid, or a mixture thereof.

The cannabinoid composition may comprise a cannabinoid and a terpene. The terpene may be alpha bisabolol, alpha phellandrene, alpha pinene, beta caryophyllene, beta pinene, cadinene, camphene, camphor, citral, citronellol, delta 3 carene, eucalyptol, eugenol, gamma terpinene, geraniol, humulene, limonene, linalool, nerol, nerolidol, ocimene, para-cymene, phytol, pulegone, terpineol, terpinolene, valencene, or a mixture thereof.

The cannabinoid composition may be substantially free of lipids. The cannabinoid composition may comprise less than 1% lipids by weight.

The cannabinoid-binding agent mixture may be substantially free of pesticides, fungicides, fertilizers, plant material, organelles, nucleic acids, lignin, and mixtures thereof. The cannabinoid-binding agent mixture may comprise less than 1% w/w of pesticides, fungicides, fertilizers, plant material, organelles, nucleic acids, lignin, and mixtures thereof.

The cannabinoid-binding agent mixture may comprise less than 0.5%, 0.1%, 0.01%, or 0.001% w/w pesticides, fungicides, fertilizers, plant material, organelles, nucleic acids, lignin, and mixtures thereof.

The cannabinoid-binding agent mixture may comprise a concentration of pesticides or fungicides ranging from about 0 ppm to 10 ppm.

In reference to FIG. 1A, depicts an exemplary cannabinoid extrusion system 100. The cannabinoid extract comprising a cannabinoid acid 103 is passed through a heat transfer screw conveyor 101 for 90° C. to 130° C. for 1-60 minutes. The heat transfer screw conveyor does not allow the ventilation of the $CO_2$ produced, instead, the $CO_2$ produced from decarboxylation serves as a foaming agent 109 to create a heated cannabinoid foam. Alternatively, an extraneous foaming agent 109 may be adding, including but not limited to a blowing agent, including but not limited to carbon dioxide ($CO_2$), pentane, chlorofluorocarbons, or a mixture thereof. The heat transfer screw conveyor is coupled to a solution tube 104 where an anti-solvent, e.g., cold pentane at about −20° C. to 0° C., is passed over the heated cannabinoid foam. The cold anti-solvent (e.g., pentane at about −20° C. to 0° C.) is fed in at the proximal end where the heated cannabinoid foam 110 is extruded from the heat transfer screw conveyor and runs along the length of the heated cannabinoid foam, allowing the foaming agent (e.g., $CO_2$) to vent 105 and allowing the anti-solvent (e.g., pentane) to absorb terpenes 107. At the distal end, a cooled, cannabinoid crystal, substantially free of terpenes is extruded 110. The cannabinoid crystal may be a cannabidiol crystal substantially free of terpenes. The anti-solvent is collected, chilled, and recycled into the solution tube 104 by means of an anti-solvent storage and chilling tank 106. In an embodiment, a sonication device 111 is positioned at the distal end of the heat screw conveyor 101 to disrupt the cannabinoid crystal product, e.g., sonically disrupt the crystal into smaller pieces. The sonication device may be an array of sonication devices. The crystals may be sonicated in bath of anti-solvent. The comminuted cannabinoid crystals may be washed, and the anti-solvent and crystal collected. The solvent may be collected by means of filtration (including membrane filtration, mesh, screen, filter, or a combination thereof). The cannabinoid crystal product may be recovered from the filtration step and washed, including with anti-solvent or a solvent. For example, the cannabinoid crystal product may be filtered (including using a membrane) to recover the solvent.

Figure 1B:
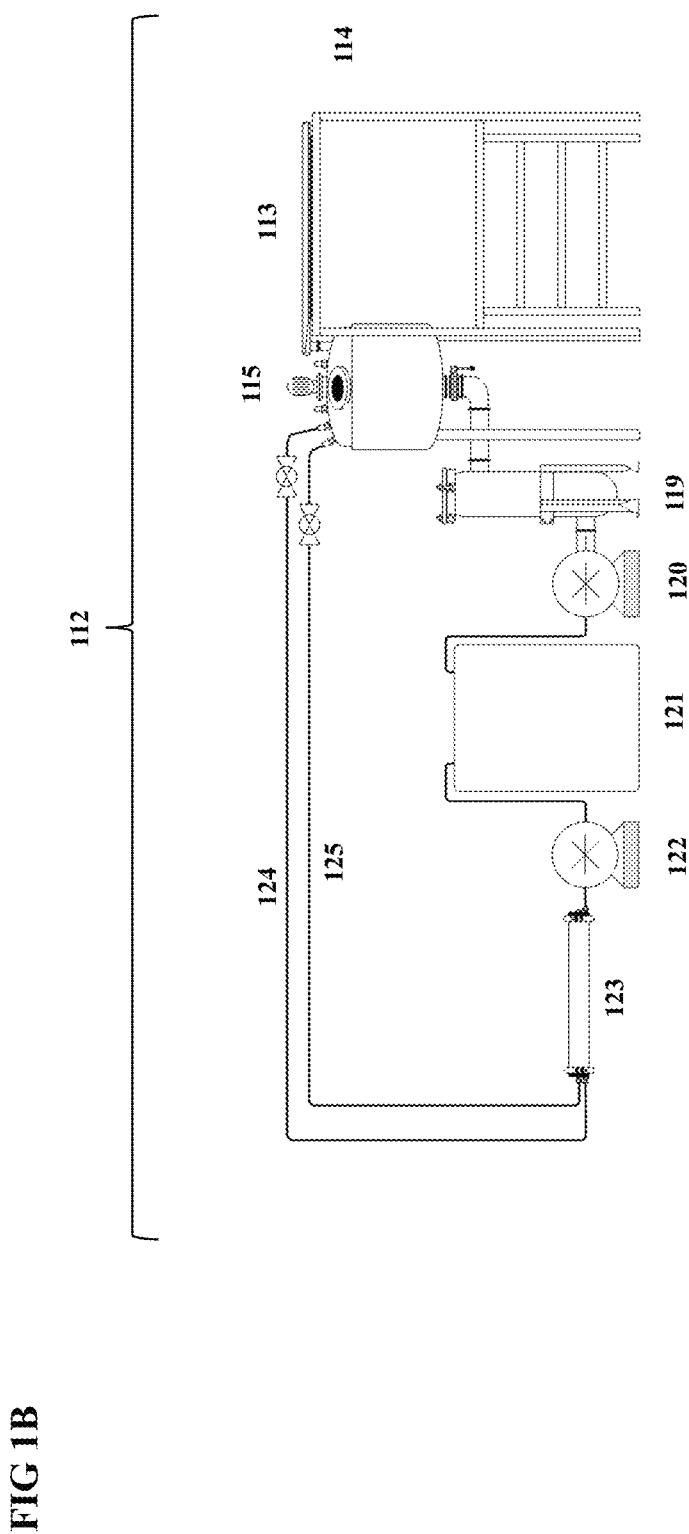

In reference to FIG. 1B, a system for extracting a cannabinoid 112 comprising a heated platform 113 with an elevated personnel platform 114 configured to move heated product into a crystallization vessel 115, wherein the crystallization vessel is configured with a first solvent input 116, a second solvent input 117, a nucleating agent input (optional), heat product input, and further comprising agitation means, coupled to a filtration means 119 (coupled to a diaphragm pump 120) means coupled to a solvent storage means 121 coupled to membrane filtration means 122 (with a high pressure solvent pump 123), wherein the membrane filtration 124 means comprises a first solvent output 124 and a second solvent output 125.

Figure 1C:
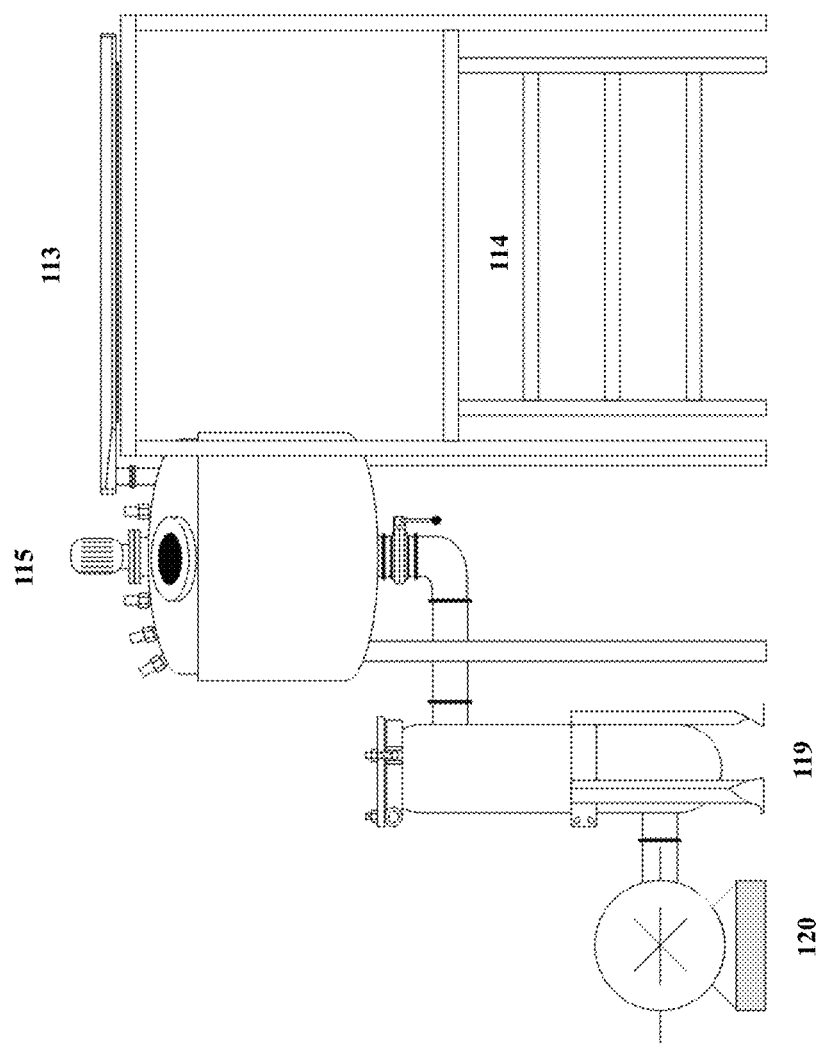

In reference to FIG. 1C, a system for extracting a cannabinoid 112 comprising a heated platform 113 with an elevated personnel platform 114 configured to move heated product into a crystallization vessel 115, wherein the crystallization vessel is coupled to a filtration means 119 coupled to a diaphragm pump 120. This allows for collection of the crystals by means of filtration. The filter may have a pore size of about 0.1 µm to 10 µm.

Figure 2:
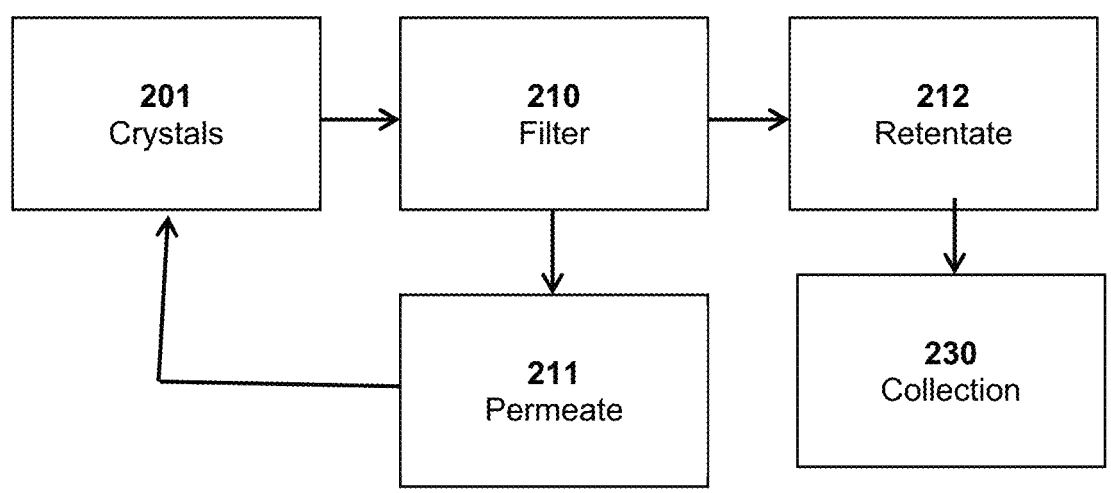
FIG. 2 is a flow-chart filtering the cannabinoid crystal slurry according to the disclosure.

Another method is shown in the flow chart of FIG. 2. Crystallization may be performed by as described herein. The cannabinoid crystals 201 collected from the crystallization is subjected to a filtration step 210, the solvent passes through a membrane. The retentate 212 comprises the cannabinoid crystals. The permeate 211 may be recycled back into crystallization or used to wash more cannabinoid crystals.

Figure 3:
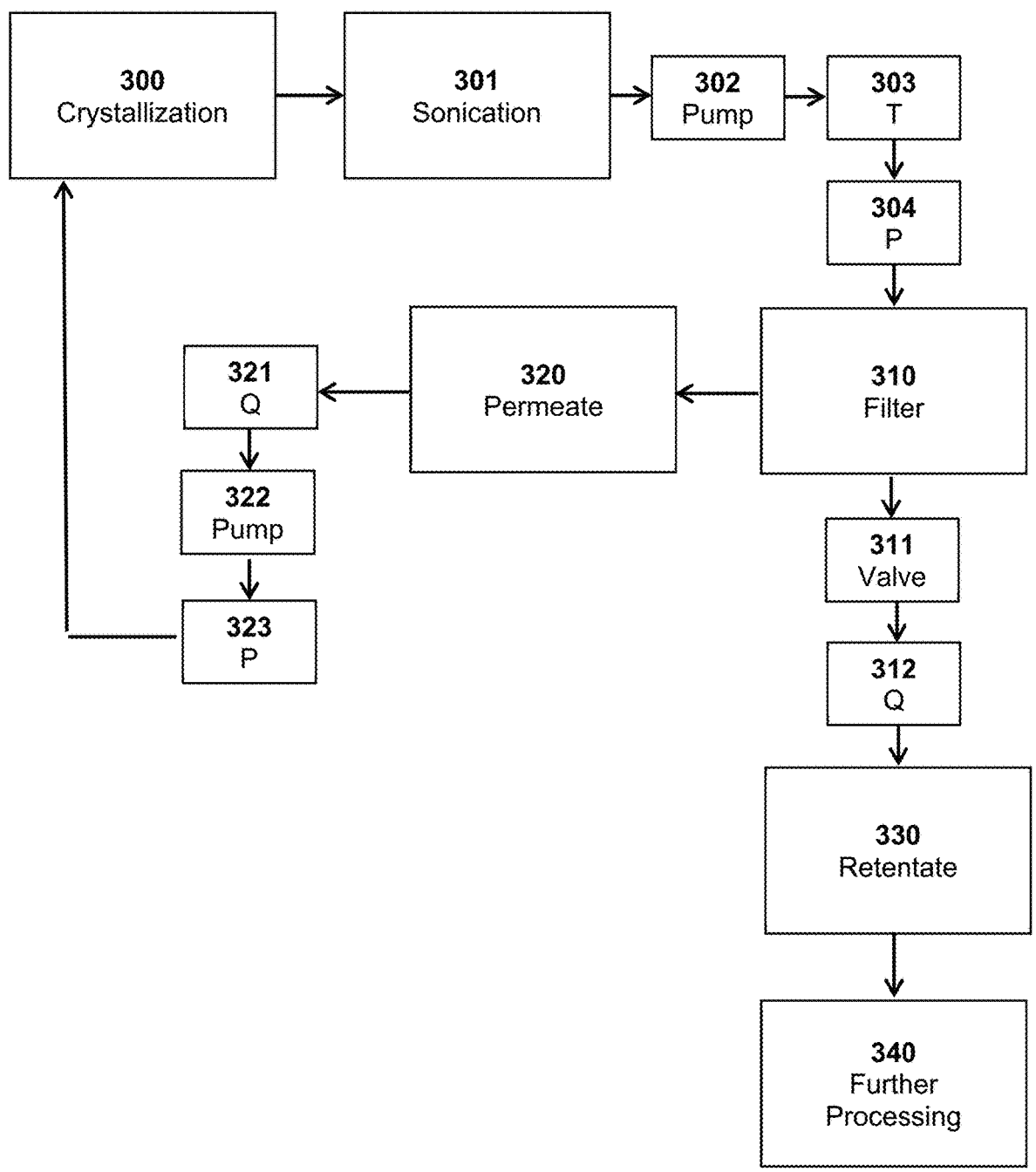
FIG. 3 is a flow-chart filtering the cannabinoid crystal slurry according to the disclosure.

FIG. 3 shows another method of isolating cannabinoid crystals after crystallization 300 described herein. The crystals may be subjected to sonication to break up the crystals creating a crystal slurry 301 that is pumped using pump 302, the temperature of the slurry is measured using temperature gauge 303, and the pressure is measured using pressure gauge 304. Slurry 301 is then subjected to filtration step 310. Retentate 330, including captured cannabinoid crystals, flows through back pressure valve 311, and flowmeter 312. Flowmeter 321 is used to measure the flow rate (Q) of permeate 320, including the solvent. Pump 323 pumps permeate 320, and pressure gauge 323 measures the pressure of permeate it is recycled into crystallization 300. Retentate 330 flows through back pressure valve 311, and the flow rate of retentate 312 is measured using flowmeter 312. The retentate comprising the cannabinoid crystals may be collected for further processing.

Figure 4:
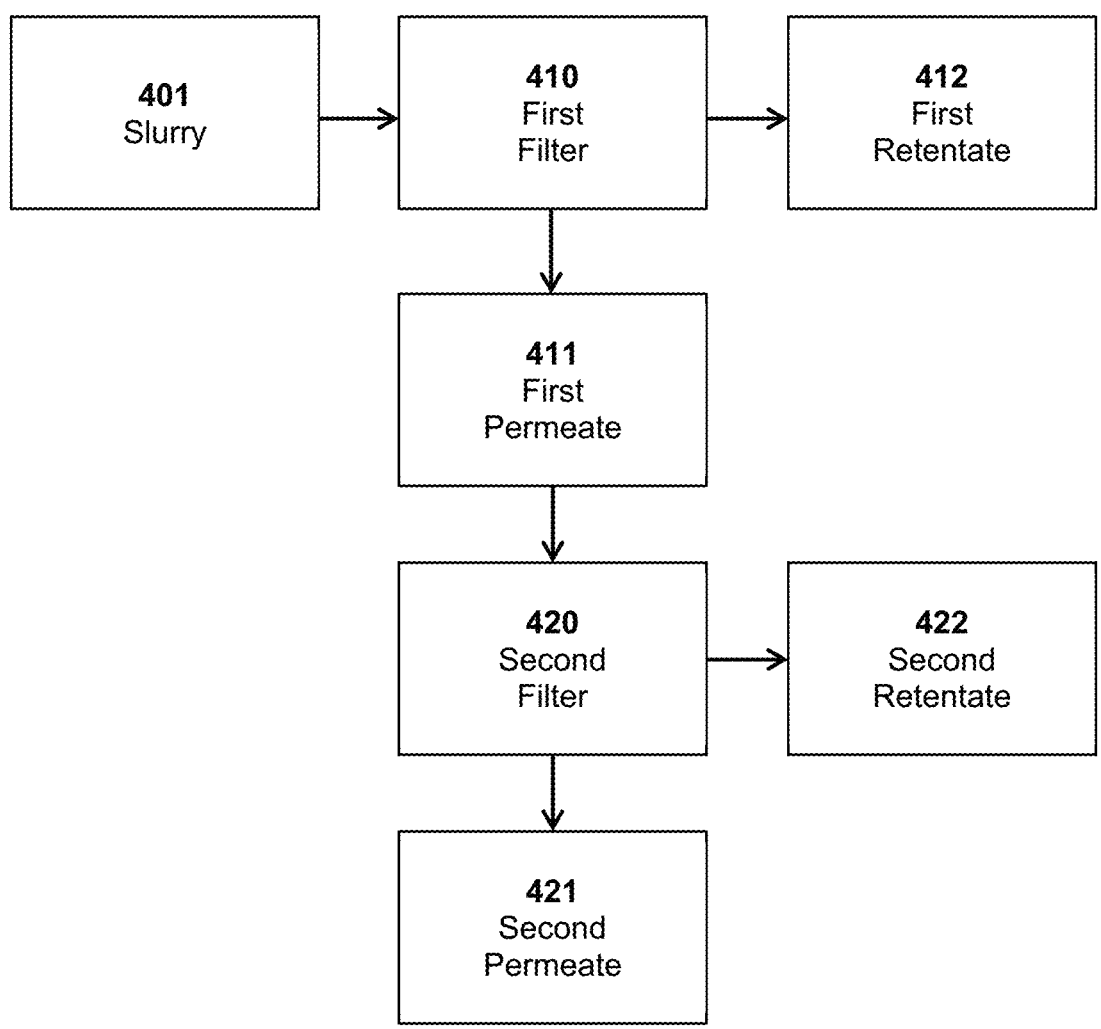
FIG. 4 depicts an exemplary flow-chart filtering the cannabinoid crystal slurry.

In FIG. 4, the method includes subjecting slurry 401 as described herein to filtration 410. First retentate 412 comprises the cannabinoid-chitosan crystals. The first retentate 412 may be collected and washed with water prior to further processing. The solvent and anti-solvent flow through the first membrane with the first permeate 411. The first permeate 411 is then subjected to filtration 420 through the second membrane to yield second retentate 422 in which the solvent is concentrated. Second permeate 421 includes the recovered antisolvent (water).

Figure 5:
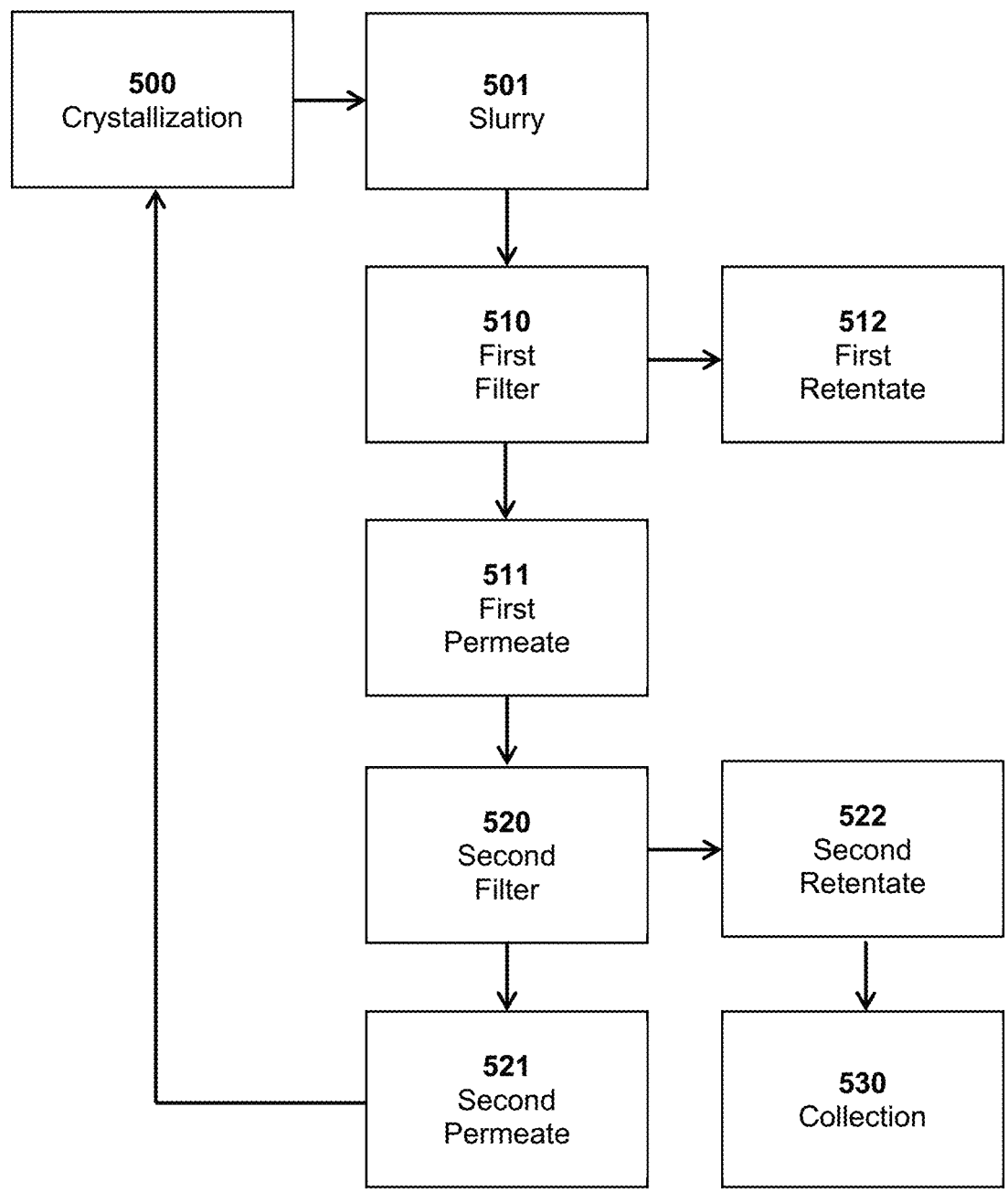
FIG. 5 depicts an exemplary flow-chart filtering the cannabinoid crystal slurry.

Another exemplary method is shown in the flow chart of FIG. 5. Crystallization 500 may be performed by as described herein. The slurry is collected from the crystallization vessel is subjected to a filtration step 510, the solvent/anti-solvent 501 passes through a first membrane. First retentate 512 comprises the cannabinoid crystals. The first permeate 511 is then subjected to filtration 520 through the second membrane to yield second retentate 522 comprising the solvent. The second permeate 521 includes the recovered antisolvent (water), which may be recycled back into crystallization 500.

Figure 6:
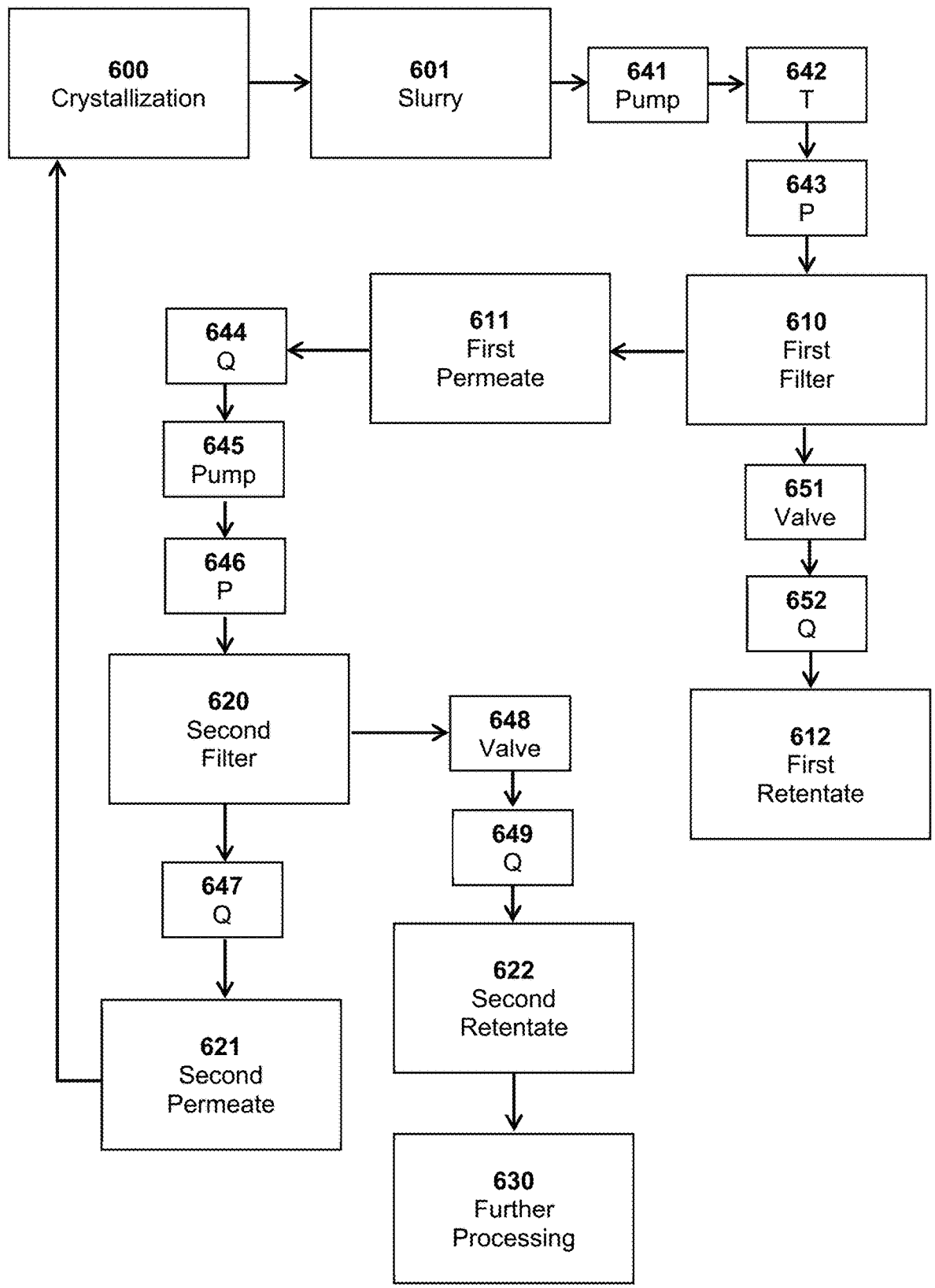
FIG. 6 depicts an exemplary flow-chart filtering the cannabinoid crystal slurry.

FIG. 6 shows another exemplary method of isolating cannabinoid crystals after crystallization 600 described herein. The resulting slurry 601 is pumped using pump 641, the temperature of the slurry is measured using temperature gauge 642, and the pressure is measured using pressure gauge 643. Slurry 601 is then subjected to filtration step 610. First retentate 612, including captured cannabinoid crystals, flows through back pressure valve 651, and flowmeter 652. Flowmeter 644 is used to measure the flow rate (Q) of first permeate 611, including the solvent and anti-solvent. Pump 645 pumps first permeate 611, and pressure gauge 646 measures the pressure of first permeate 611 before it is subjected to the second filtration step 620. Flowmeter 647 measures the flow rate of second permeate 621, which includes the recovered antisolvent (water) and is recycled into crystallization 600. Second retentate 622 flows through back pressure valve 648, and the flow rate of second retentate 622 is measured using flowmeter 649. Second retentate comprising the solvent may be collected for further processing.

Further embodiments of the present invention will now be described with reference to the following examples. The examples contained herein are offered by way of illustration and not by any way of limitation.

EXAMPLES

The methods described herein will now be described with reference to the following examples. The examples contained herein are offered by way of illustration and not by any way of limitation.

Definitions

Unless defined otherwise, all technical and scientific terms used herein have the same meaning as those commonly understood by one of ordinary skill in the art.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In the methods described herein, the steps can be carried out in any order without departing from the principles of this disclosure, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

"Cannabidiol acid," as used herein, refers broadly to the chemical precursor of cannabidiol. This is also referred to as cannabidiol acetate, or CBDA in the art:

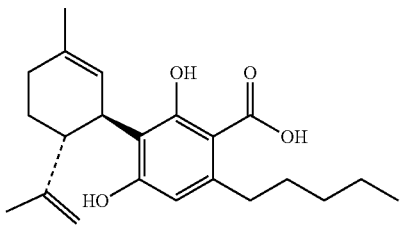 [SMILES: C=C(C)[C@@H]1CCC(C)=C[C@H]1c1c(O)cc(CCCCC)c(C(=O)O)c1O]

CBDA is heated to decarboxylate and form cannabidiol (CBD).

"Cannabinoid acid," as used herein, refers broadly to the chemical precursor of the physiologically active form of the cannabinoid (e.g., the decarboxylated form).

"Cannabis plant material," "cannabis," and "cannabis material," as used herein, refers broadly to any cannabis plant or part thereof, this includes but is not limited to, flowers, stems, nodes, leaves, pistils, colas, calyxs, trichomes, seed, stalk, buds (including dormant buds, axillary buds, and terminal buds), petiole, rachis, bract, and roots. Cannabis plant material also refers broadly to hemp that includes but is not limited to cannabis plants with less than 0.3% THC content. Hemp and industrial hemp can be used interchangeably as both refer to cannabis plants with less than 0.3% THC content.

"Cannabis," as used herein, refers broadly to all plants of the genus cannabis and/or the family cannabaceae, including but not limited to all plants of the species *Cannabis sativa*, *cannabis indica*, and *Cannabis ruderalis*. Hybrids, clones, cultivars, and varieties are also included. *Cannabis* also broadly includes hemp.

"*Cannabis* extract," as used herein, refers broadly to any composition comprising a cannabinoid. *Cannabis* extracts may also comprise lipids, terpenes, solvent, or mixtures thereof.

"Cannabinoid acid," as used herein, refers broadly to a cannabinoid prior to decarboxylation. Cannabinoid acids, including but not limited to cannabigerolic acid, cannabidiol acid (CBDA), Δ9-tetrahydrocannabinolic acid (THCA), cannabidiolic acid, cannabichromenenic acid, cannabigerovarinic acid, tetrahydrocanabivarinic acid, cannabidivarinic acid, cannabichromevarinic acid, or a mixture thereof. Cannabinoid acids generally have low physiological activity as compared to their decarboxylated form, e.g., cannabidiol acid (CBDA) versus cannabidiol (CBD).

"Lipids," as used herein, refers broadly to waxes, gums, fats, and mixtures thereof. The term also encompasses mono-, di- and triacylglycerols, phospholipids, free fatty acids, fatty alcohols, cholesterol, cholesterol esters, and the like. The term "fatty acid" refers to a carboxylic acid with a long aliphatic tail of at least 8, at least 10, at least 12, at least 16, at least 18 or at least 22 carbon atoms in length, either saturated or unsaturated. Examples of fatty acids include linear fatty acids of $C_6$-$C_{24}$ such as caproic acid, caprylic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid, erucic acid, and mixtures thereof.

"Phospholipid" as used herein refers to a glycerol phosphate with an organic headgroup such as choline, serine, ethanolamine or inositol and zero, one or two (typically one or two) fatty acids esterified to the glycerol backbone. Phospholipids include, but are not limited to, phosphatidylserine, phosphatidylglycerol, phosphatidylcholine, phosphatidylethanolamine, phosphatidylserine, phosphatidylinositol, and diphosphatidylglycerol as well as corresponding lysophospholipids.

"Molecular weight cutoff," as used herein, refers broadly to the minimum molecular weight of a solute that is 90% retained by a membrane. See, e.g., K. J. Kim et al., Journal of Membrane Science 87: 35-46 (1994) using dextran and a transmembrane pressure of 50 kPa.

"Winterize," as used herein, refers broadly to any process by which lipids are removed from a cannabis product. Winterization refers broadly to any process that remove lipids from a cannabis product.

Although the subject matter disclosed herein has been described in some detail by way of illustration and example for purposes of clarity of understanding, it should be understood that certain changes and modifications can be practiced within the scope of the appended claims. Modifications of the above-described methods would be understood in view of the foregoing disclosure or made apparent with routine practice or implementation of the described methods to persons of skill in extraction chemistry; extraction processing, mechanical engineering, and/or related fields are intended to be within the scope of the following claims.

All publications (e.g., non-patent literature), patents, patent application publications, and patent applications mentioned in this specification are indicative of the level of skill of those skilled in the art to which this disclosure pertains. All such publications (e.g., non-patent literature), patents, patent application publications, and patent applications are herein incorporated by reference to the same extent as if each individual publication, patent, patent application publication, or patent application was specifically and individually indicated to be incorporated by reference.

While the foregoing methods have been described in connection with this disclosure, it is not to be limited thereby but is to be limited solely by the scope of the claims which follow.

I claim:

1. A method for decarboxylating and crystallizing a cannabinoid comprising
   providing a cannabinoid extract comprising a cannabinoid to a heat transfer screw at a sufficient temperature;
   moving the heated cannabinoid extract through the heat transfer screw;
   introducing a foaming agent to produce a cannabinoid foam;
   extruding the heated cannabinoid foam into a vessel and passing an anti-solvent at a temperature of −20° C. to 20° C. over the heated cannabinoid foam forming a cannabinoid crystal; and
   recovering the cannabinoid crystal.

2. The method of claim 1, wherein the foaming agent is a blowing agent.

3. The method of claim 2, wherein the foaming agent is carbon dioxide ($CO_2$), pentane, butane, chlorofluorocarbons, or a mixture thereof.

4. The method of claim 1, wherein the foaming agent is carbon dioxide ($CO_2$) produced in situ by decarboxylation of a cannabinoid acid.

5. The method of claim 1, wherein the anti-solvent is pentane, butane, propane, or hexane.

6. The method of claim 1, wherein the anti-solvent extracts terpenes from the cannabinoid foam.

7. The method of claim 1, wherein the cannabinoid extract is provided by means of spraying, pouring, injection, or a combination thereof.

8. The method of claim 1, wherein the cannabinoid crystals are substantially free of lipids.

9. The method of claim 1, wherein the method further comprises collecting the terpenes.

10. A system for decarboxylating a cannabinoid comprising:
    a heat transfer screw heat configured to be heated to a sufficient temperature;
    a means for adding a foaming agent to the heat transfer screw;
    in fluid connection with a vessel configured to pass anti-solvent at a temperature of −20° C. to 20° C. from the proximal end of the heat transfer screw to the distal end, and means for collecting the anti-solvent.

* * * * *